US011453362B2

(12) United States Patent
Nebuya

(10) Patent No.: US 11,453,362 B2
(45) Date of Patent: Sep. 27, 2022

(54) DETECTION APPARATUS, SEAT BELT, AND MONITORING SYSTEM

(71) Applicant: POSH WELLNESS LABORATORY INC., Tokyo (JP)

(72) Inventor: Satoru Nebuya, Tokyo (JP)

(73) Assignee: POSH WELLNESS LABORATORY, INC., Tokyo (JP)

( * ) Notice: Subject to any disclaimer, the term of this patent is extended or adjusted under 35 U.S.C. 154(b) by 0 days.

(21) Appl. No.: 17/150,596

(22) Filed: Jan. 15, 2021

(65) Prior Publication Data

US 2021/0206345 A1 Jul. 8, 2021

Related U.S. Application Data

(63) Continuation of application No. PCT/JP2019/001102, filed on Jan. 16, 2019.

(30) Foreign Application Priority Data

Jul. 19, 2018 (WO) .................. PCT/JP2018/027196

(51) Int. Cl.
*B60R 22/48* (2006.01)
*G01B 7/28* (2006.01)
(Continued)

(52) U.S. Cl.
CPC .............. *B60R 22/48* (2013.01); *A61B 5/256* (2021.01); *G01B 7/28* (2013.01); *A61B 5/0295* (2013.01);
(Continued)

(58) Field of Classification Search
CPC ......... B60R 22/48; B60R 22/485; G01B 7/28; G01L 1/14; G01L 1/18; G01L 1/20;
(Continued)

(56) References Cited

U.S. PATENT DOCUMENTS

2003/0216630 A1   11/2003 Jersey et al.
2004/0189340 A1*  9/2004 Okada .................. G01P 15/123
                                                              73/1.38
(Continued)

FOREIGN PATENT DOCUMENTS

EP     3207814 A1      8/2017
JP     H08-140952 A    6/1996
(Continued)

OTHER PUBLICATIONS

NPL Search (Feb. 7, 2022).*
(Continued)

*Primary Examiner* — Van T Trieu
(74) *Attorney, Agent, or Firm* — Rankin, Hill & Clark LLP

(57) ABSTRACT

This detection device is a device for detecting the movement of a human body. The detection device has: a substrate having flexibility; an electric element provided on the substrate and having an electrical characteristic that changes with the movement of the human body; and a semiconductor element that is provided on the substrate, detects a change in the electrical characteristic of the electric element, and outputs a detection value corresponding to the detected result. The substrate is a flexible substrate or a fabric member including conductive fibers, for example.

17 Claims, 24 Drawing Sheets

(51) Int. Cl.
  *A61B 5/256* (2021.01)
  *A61B 5/0295* (2006.01)
  *A61B 5/113* (2006.01)
  *B60R 22/12* (2006.01)

(52) U.S. Cl.
  CPC ............... *A61B 5/113* (2013.01); *B60R 22/12* (2013.01); *B60R 2022/485* (2013.01)

(58) Field of Classification Search
  CPC ..... G01L 1/22; G01L 5/00; G01L 5/16; G01L 5/162; G06F 3/041; G06F 3/0416; G06F 3/0418; G06F 3/044; G06F 3/0446
  See application file for complete search history.

(56) References Cited

U.S. PATENT DOCUMENTS

| | | |
|---|---|---|
| 2006/0058694 A1 | 3/2006 | Clark et al. |
| 2006/0155175 A1 | 7/2006 | Ogino et al. |
| 2008/0066564 A1* | 3/2008 | Hayakawa ............... G01L 1/20 73/862.628 |
| 2014/0343392 A1 | 11/2014 | Yang |
| 2015/0060255 A1* | 3/2015 | Chen ............... H03K 17/9622 200/5 R |
| 2016/0287177 A1 | 10/2016 | Huppert et al. |
| 2016/0302690 A1 | 10/2016 | Nebuya et al. |
| 2016/0365029 A1 | 12/2016 | Yamazaki et al. |
| 2017/0296128 A1 | 10/2017 | Aoki |
| 2017/0330437 A1 | 11/2017 | Hatanaka et al. |
| 2018/0348235 A1 | 12/2018 | Vigue et al. |
| 2018/0364840 A1* | 12/2018 | Alack, Jr. ............... G06F 1/163 |
| 2020/0200617 A1* | 6/2020 | Toyoshima ............... G01L 5/00 |

FOREIGN PATENT DOCUMENTS

| | | |
|---|---|---|
| JP | 2009-108451 A | 5/2009 |
| JP | 2014-233619 A | 12/2014 |
| JP | 2015-077270 A | 4/2015 |
| JP | 2017-019342 A | 1/2017 |
| JP | 2017-500093 A | 1/2017 |
| JP | 2017-136304 A | 8/2017 |
| JP | 2018-050944 A | 4/2018 |
| JP | 2018-121700 A | 8/2018 |
| WO | 2015/002210 A1 | 1/2015 |
| WO | 2016/060222 A1 | 4/2016 |
| WO | 2017/089474 A1 | 6/2017 |

OTHER PUBLICATIONS

International Search Report dated Jan. 8, 2019, PCT/JP2018/027196, 4 pages.
International Preliminary Report on Patentability with Written Opinion dated Jan. 19, 2021, PCT/JP2018/027196, 13 pages.
International Search Report dated Apr. 23, 2019, PCT/JP2019/001102, 4 pages.
International Preliminary Report on Patentability with Written Opinion dated Jan. 19, 2021, PCT/JP2019/001102, 19 pages.
International Search Report dated Sep. 24, 2019, PCT/JP2019/028462, 4 pages.
International Preliminary Report on Patentability with Written Opinion dated Jan. 19, 2021, PCT/JP2019/028462, 22 pages.
Kitaoka, et al., "Infusion Treatment for Dehydration", Journal of Clinical and Experimental Medicine, vol. 140, No. 5, pp. 275-279, with partial English Translation, Cited in ISR of PCT/JP2019/028462; 7 pages.
European Search Report, Application No. 19837292.2, dated Aug. 13, 2021, 9 pages.
European Search Report, Application No. 19837341.7, dated Aug. 10, 2021, 12 pages.

* cited by examiner

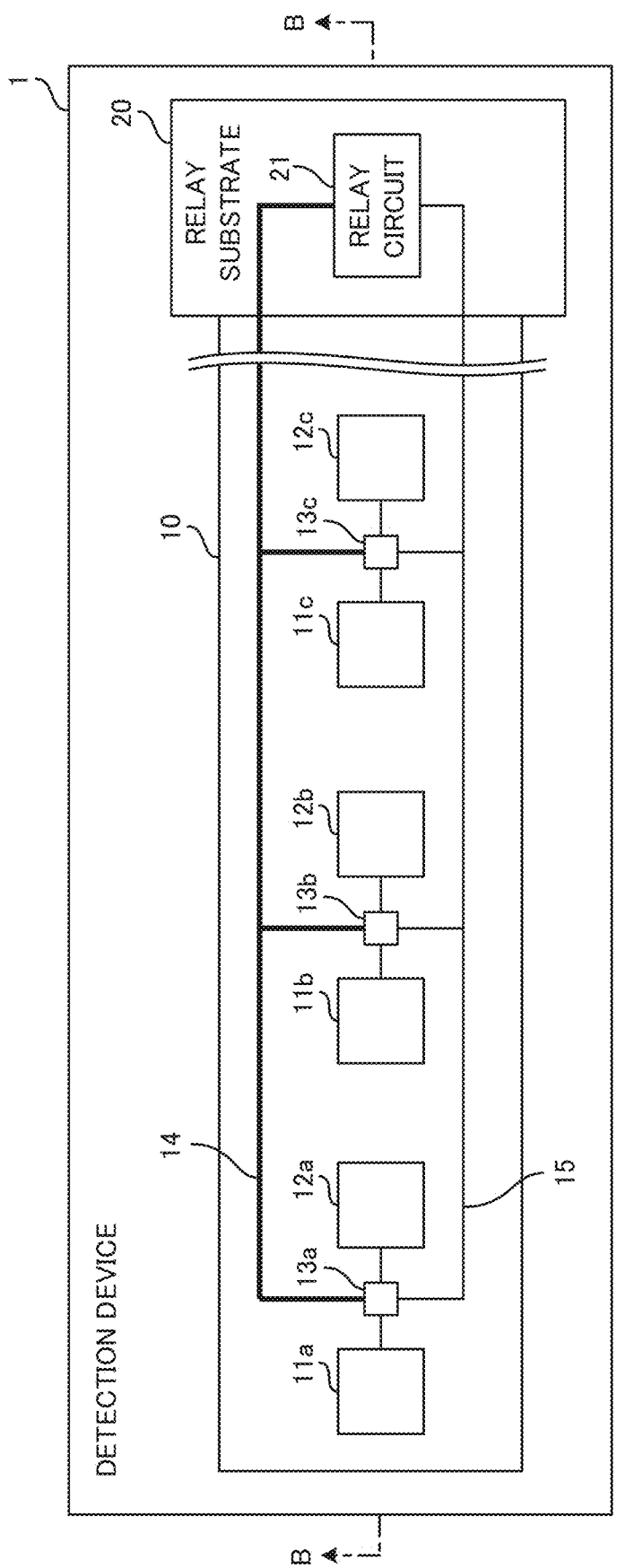
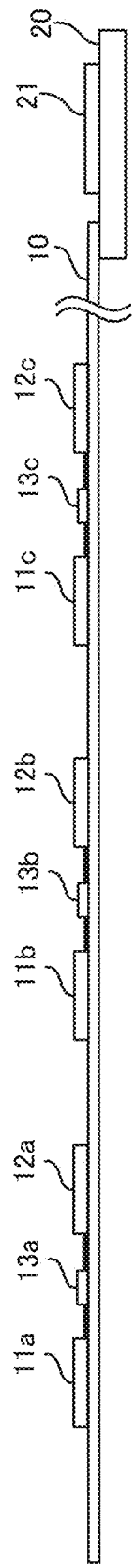
FIG. 3A
FIG. 3B

DETECTION APPARATUS, SEAT BELT, AND MONITORING SYSTEM

CROSS-REFERENCE TO RELATED APPLICATIONS

The present application is a continuation application of International Application number PCT/JP2019/001102, filed on Jan. 16, 2019, which claims priority under 35 U.S.C. § 119(a) to PCT Patent Application number PCT/JP2018/027196, filed on Jul. 19, 2018. The contents of these applications are incorporated herein by reference in their entirety.

BACKGROUND OF THE DISCLOSURE

The present disclosure relates to a detection device, a seat belt, and a monitoring system for detecting a state of a living body. Conventionally, there has been known a technique of sending a weak current from an electrode pair attached to a body surface, and imaging a conductivity distribution or a change in the conductivity distribution in a living body from a potential difference generated on the body surface. Japanese Unexamined Patent Application Publication No. 2017-136304 discloses a driver monitoring device capable of monitoring a state of a driver of a vehicle by applying an Electrical Impedance Tomography (hereinafter, EIT) technique to a seat belt.

In the prior art, each electrode is connected to a measurement circuit provided near the end of the seat belt, and the measurement circuit relays electrical signals transmitted and received between the driver monitoring device and the electrode. However, since the seat belt has a long shape and is approximately three meters long, there is a problem that noise, which causes deterioration of the measurement accuracy, is easily superimposed between the electrode and the measurement circuit during the transmission of the electrical signal. There is also a further challenge that more precise measurements are required to accurately monitor the driver's health condition while driving, and reduction of noise is an urgent issue in order to cope with this challenge.

BRIEF SUMMARY OF THE DISCLOSURE

The present disclosure focuses on these points, and an object of the present disclosure is to improve accuracy in detecting a state of a living body.

The first aspect of the present disclosure is a detection device for detecting movement of a human body. The detection device includes a base material that has flexibility, an electric element that is provided on the base material and whose electrical characteristics change according to the movement of the human body, a semiconductor element that is provided on the base material, detects a change in the electrical characteristics of the electric element, and outputs a detection value corresponding to the detected result.

The second aspect of the present disclosure is a seat belt mounted on a vehicle. The seat belt includes a strip-shaped front-side belt, a reverse-side belt that is coupled with the front-side belt, and a detection device that is provided between the front-side belt and the reverse-side belt, wherein the detection device includes a base material that has flexibility, an electric element that is provided on the base material, and whose electrical characteristics change according to movement of a human body, and a semiconductor element that is provided on the base material, detects a change in the electrical characteristics of the electric element, and outputs a detection value corresponding to the detected result.

The third aspect of the present disclosure is a monitoring system. The monitoring system includes a detection device that detects a state of a person wearing a seat belt mounted on a vehicle, and a monitoring device that controls the vehicle on the basis of the state of the person detected by the detection device, wherein the detection device includes a base material that has flexibility, an electric element that is provided on the base material, and whose electrical characteristics change according to the movement of the human body, a semiconductor element that is provided on the base material, detects a change in the electrical characteristics of the electric element, and outputs a detection value corresponding to the detected result, and a transmission part that transmits a signal including the detection value outputted by the semiconductor element to the monitoring device.

BRIEF DESCRIPTION OF THE DRAWINGS

FIGS. 3A and 3B each schematically show a configuration of a detection device.

DETAILED DESCRIPTION OF THE DISCLOSURE

Hereinafter, the present invention will be described through exemplary embodiments of the present invention, but the following exemplary embodiments do not limit the invention according to the claims, and not all of the combinations of features described in the exemplary embodiments are necessarily essential to the solution means of the invention.

First Embodiment

[An Outline of a Monitoring System S]

Figure 1:
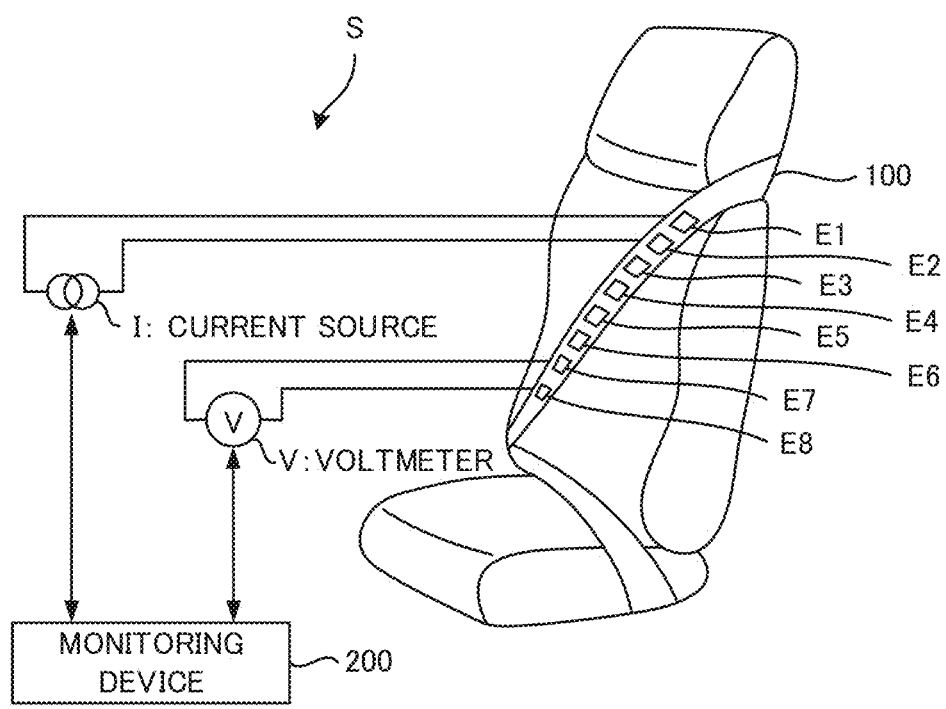
FIG. 1 is a diagram for explaining an outline of a monitoring system.

FIG. 1 is a diagram for explaining an outline of a monitoring system S. The monitoring system S is a system for monitoring a state of a person in a vehicle, such as a driver and an occupant, and includes a seat belt 100 and a monitoring device 200. The monitoring system S generates an electric field by using an electrode pair E provided in the seat belt 100 and measures a potential difference among a plurality of electrodes included in the electrode pair E while generating the electric field to identify a state of a body of a person in a car. In the following description, a case where a person in a vehicle is a driver is described as an example, but the embodiment disclosed herein can be applied to a case where a person other than the driver wears the seat belt 100.

Figure 2A:
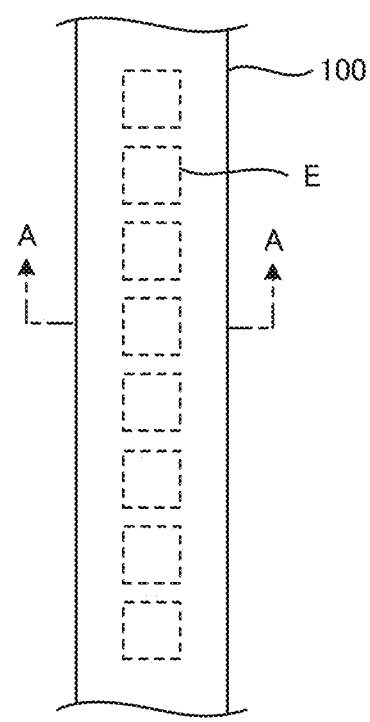
FIGS. 2A and 2B are each a schematic diagram showing a shape of a seat belt.
Figure 2B:
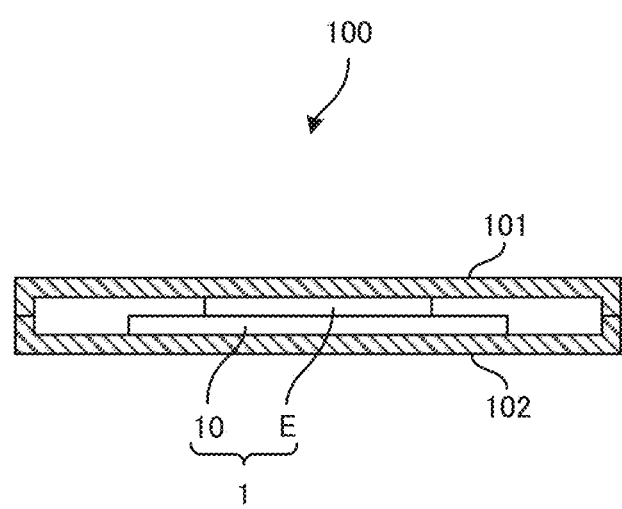

FIGS. 2A and 2B are each a schematic diagram showing a shape of the seat belt 100. FIG. 2A is a plane figure of the seat belt 100, and FIG. 2B shows an A-A-line cross section of the seat belt 100. The seat belt 100 includes a strip-shaped front-side belt 101, a reverse-side belt 102 coupled with the front-side belt 101, and a detection device 1 provided between the front-side belt 101 and the reverse-side belt 102. The detection device 1 is a sheet-like device that detects the intensity of the electric field near the driver's body. The detection device 1 includes a plurality of electrode pairs E (E1-E8 in FIG. 1) that generates the electric field and is provided on a flexible substrate 10, which is an example of a base material having flexibility.

The electrode pair E is an example of an electric element whose electrical characteristics change according to a movement of a person wearing the seat belt 100. The impedance in the vicinity of the electrode pair E changes according to the movement based on the state of the body, such as breathing or a heartbeat, of the person wearing the seat belt 100. As a result, the state of the electric field generated by the electrode pair E changes, and so the potential difference between the plurality of electrodes constituting the electrode pair E changes.

Although described later in detail, a detection IC, which is a semiconductor element for detecting a change in the electrical characteristics of the electrode pair E, is provided in the vicinity of each electrode pair E in the flexible substrate 10. For example, the detection IC detects a change in the impedance between the plurality of electrodes constituting the electrode pair E to output a detection value indicating a change in the intensity of the electric field in the vicinity of the electrode pair E. The detection device 1 outputs, to the monitoring device 200, an electric field intensity detection value indicating a value corresponding to the intensity of the electric field detected by the detection IC. The electric field intensity detection value is not limited to the value of the intensity of the electric field itself, and can be any value as long as it is a value that changes according to the electric field intensity, such as an impedance value or a combination of a current value and a resistance value. The detection device 1 may output a signal processed or treated on the basis of the intensity of the electric field to the monitoring device 200.

The monitoring device 200 is an Engine Control Unit (ECU) having, for example, a Central Processing Unit (CPU), a Read Only Memory (ROM), a Random Access Memory (RAM), and the like. The monitoring device 200 analyzes the electric field intensity detection value inputted from the detection device 1 to identify the state of the driver's body. The monitoring device 200 identifies the state of the driver's body by calculating the impedance between a positive electrode 11 and a negative electrode 12 on the basis of, for example, i) a value of the potential difference between the positive electrode 11 and the negative electrode 12 obtained as the electric field intensity detection value and ii) a value of the current flowing through the positive electrode 11. The monitoring device 200 controls the vehicle on the basis of the identified state of the body. For example, if the monitoring device 200 identifies that the driver's heart has stopped beating, the monitoring device 200 performs control to stop the engine of the vehicle. The monitoring device 200 may store the electric field intensity detection value in a storage medium in association with the time.

[A Configuration of the Detection Device 1]

FIGS. 3A and 3B each schematically show a configuration of the detection device 1. FIG. 3A shows a perspective view of the detection device 1, and FIG. 3B is a B-B-line cross section of the detection device 1.

The detection device 1 includes the flexible substrate 10 and a relay substrate 20. The flexible substrate 10 has one end fixed to the relay substrate 20. The relay substrate 20 is, for example, a printed circuit board, and is connected to the monitoring device 200 via a cable. The relay substrate 20 is accommodated in the lower part of the seat together with the monitoring device 200, for example.

A plurality of positive electrodes 11 (a positive electrode 11a to a positive electrode 11c in FIG. 3), a plurality of negative electrodes 12 (a negative electrode 12a to a negative electrode 12c in FIG. 3), and a plurality of detection ICs 13 (a detection IC 13a to a detection IC 13c in FIG. 3) are mounted on the flexible substrate 10. The positive electrode 11a and the negative electrode 12a, the positive electrode 11b and the negative electrode 12b, and the positive electrode 11c and the negative electrode 12c each constitute an electrode pair E.

It should be noted that the detection IC 13 is provided at a position adjoining the corresponding positive electrode 11 and negative electrode 12 along the longitudinal direction of the seat belt 100 in the embodiment shown in FIG. 3, but the detection IC 13 may be provided at other positions. The detection IC 13 may be provided at, for example, a position adjoining the electrode pair E constituted by the positive electrode 11 and the negative electrode 12 corresponding to the detection IC 13 in the transverse direction of the seat belt 100. Providing the detection ICs 13 at such positions enables the electrode pairs E to be arranged in the seat belt 100 at high density, and so the resolution of the detection device 1 can be increased.

The flexible substrate 10 is provided with the plurality of detection ICs 13 corresponding to the plurality of electrode pairs E, respectively. The detection IC 13 is a semiconductor device for outputting the electric field intensity detection value corresponding to the intensity of the electric field generated between the positive electrode 11 and the negative electrode 12 included in the corresponding electrode pair E. The detection IC 13 outputs, for example, i) the value of the potential difference between the positive electrode 11 and the negative electrode 12 and ii) the value of the current flowing through the positive electrode 11, as the electric field intensity detection value.

Figure 4:
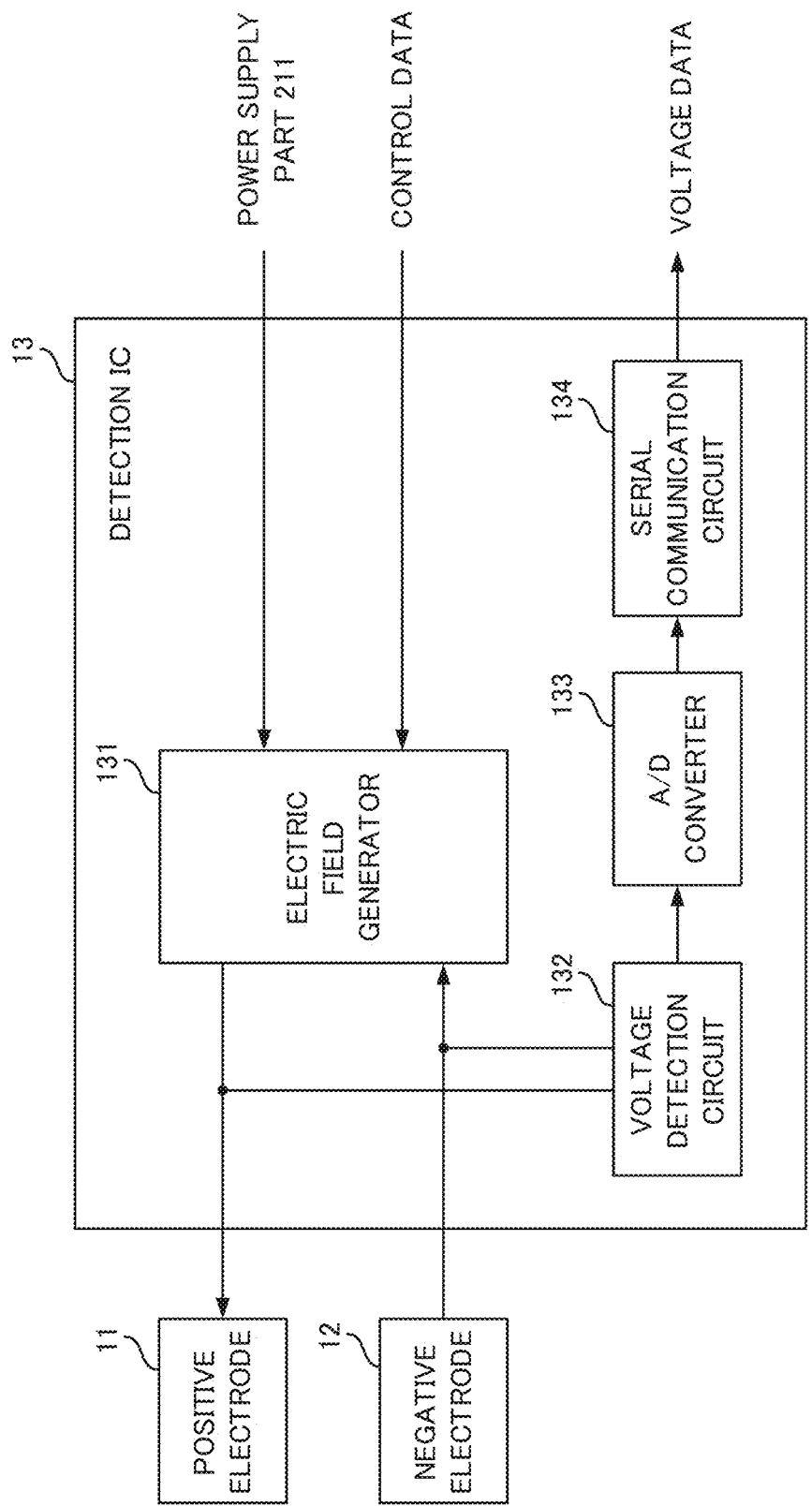
FIG. 4 shows a configuration of a detection IC.

FIG. 4 shows a configuration of the detention IC 13. The detection IC 13 includes an electric field generator 131, a voltage detection circuit 132, an A/D converter 133, and a serial communication circuit 134. The electric field generator 131 supplies a weak current to the positive electrode 11 on the basis of the power supplied from the relay substrate 20 to generate the electric field between the positive electrode 11 and the negative electrode 12. The electric field generator 131 determines the timing for supplying the weak current and the current value on the basis of, for example, control data received from the relay substrate 20.

The voltage detection circuit 132 detects the potential difference between the positive electrode 11 and the negative electrode 12 while the electric field generator 131 supplies the weak current to the positive electrode 11. The potential difference between the positive electrode 11 and the negative electrode 12 has a magnitude corresponding to the intensity of the electric field, and the greater the potential difference is, the greater the intensity of the electric field becomes. The voltage detection circuit 132 inputs a signal of a voltage corresponding to the potential difference between the positive electrode 11 and the negative electrode 12 to the A/D converter 133.

The A/D converter 133 converts the analog signal inputted from the voltage detection circuit 132 into digital data. That is, the A/D converter 133 generates digital data corresponding to a voltage value of the signal outputted by the voltage detection circuit 132. The A/D converter 133 inputs the generated digital data to the serial communication circuit 134.

The serial communication circuit 134 transmits the digital data (voltage data) inputted from the A/D converter 133 to the relay substrate 20 using a format determined by a communication method such as Serial Peripheral Interface (SPI) or Inter-Integrated Circuit (I2C) (I2C is a registered trademark).

Figure 5:
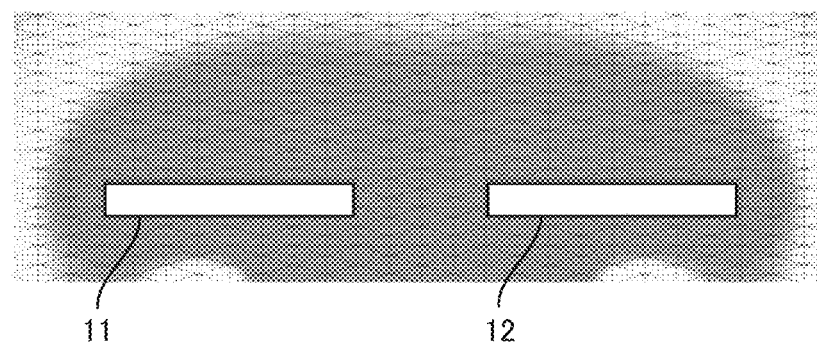
FIG. 5 shows an intensity distribution of an electric field generated around a positive electrode and a negative electrode.

FIG. 5 shows an intensity distribution of the electric field generated around the positive electrode 11 and the negative electrode 12. In FIG. 5, the electric field intensity in the dark-colored region is greater than the electric field intensity in the light-colored region. It can be seen that the strong electric field region occurs between the positive electrode 11 and the negative electrode 12 due to the electric field generator 131 supplying the weak current to the positive electrode 11.

In a state in which the driver wears the detection device 1, the driver's chest moves due to the breathing and the heartbeat of the driver. In addition, the magnitude of the current flowing in the body changes in synchronization with a) the impedance change of the blood flow due to the heartbeat or b) the impedance change of the lungs due to the breathing. As a result, the electric field generated between the positive electrode 11 and the negative electrode 12 changes in accordance with the breathing and the heartbeat of the driver. When the electric field changes, the potential difference between the positive electrode 11 and the negative electrode 12 changes. The monitoring device 200 identifies states of the breathing and the heartbeat of the driver on the basis of the change in the potential difference between the positive electrode 11 and the negative electrode 12 detected by the voltage detection circuit 132, and thereby monitors the presence/absence of an abnormal state.

Each of the plurality of detection ICs 13 is provided at a position closer to the corresponding electrode pair E thereof than to the electrode pairs E corresponding to the other detection ICs 13. Further, a plurality of distances between each of the plurality of detection ICs 13 and the electrode pairs E corresponding respectively to the plurality of detection ICs 13 are the same. That is, in a plurality of sets of a detection IC 13 and an electrode pair E, the distance between the detection IC 13 and its corresponding electrode pair E (a set of the positive electrode and the negative electrode) is constant. Said distance is a distance between, for example, a) the center position of the detection IC 13 and b) an intermediate position between the center position of the positive electrode 11 included in the electrode pair E and the center position of the negative electrode 12 included in the electrode pair E. Since the distances between each of the plurality of detection ICs 13 and the electrode pairs E corresponding to the plurality of detection ICs 13 are constant in this way, the detection sensitivity of the electric field intensity of each of the plurality of detection ICs 13 (that is, the magnitude of the electric field intensity detection value of the electric field intensity) becomes approximately the same. Therefore, the detection device 1 can detect a change in the electric field with high accuracy regardless of the position, even in the long seat belt 100.

In the flexible substrate 10, a power supply pattern 14 for supplying power to each of the plurality of detection ICs 13 and a signal pattern 15 for transmitting data outputted from each of the plurality of detection ICs to the relay substrate 20 are formed. Surfaces of the power supply pattern 14 and the signal pattern 15 are covered by resin layers having insulation properties.

Each of the plurality of detection ICs 13 transmits digital data indicating the electric field intensity detection value to the relay substrate 20 in a time-division manner via the signal pattern 15 which is the same serial signal line. The signal pattern 15 is a serial signal line capable of transmitting digital data in a serial communication method of, for example, SPI or I2C. Each of the plurality of detection ICs 13 transmits the digital data including the electric field intensity detection value to the relay substrate 20 at the time when, for example, each of the plurality of detection ICs 13 receives a command with an address of the detection IC 13 from the relay substrate 20.

The plurality of detection ICs 13 measure the potential difference between the positive electrode 11 and the negative electrode 12 simultaneously on the basis of, for example, the control signal inputted from the relay substrate 20. Each of the plurality of detection ICs 13 temporarily holds the electric field intensity detection value indicating the measured electric potential difference, until when the detection IC 13 itself transmits the electric field intensity detection value, and then transmits the digital data including the electric field intensity detection value to the monitoring device 200 via the relay substrate 20 at the timing when the detection IC 13 itself transmits the electric field intensity detection value. In this manner, the monitoring device 200 can identify, at each measurement timing, the state of the driver's body in the vicinity of a plurality of different positions in the seat belt 100 at the same time.

A relay circuit 21 is mounted on the relay substrate 20. The relay circuit 21 supplies power to each of the plurality of detection ICs 13 via the power supply pattern 14. In addition, the relay circuit 21 receives the digital data transmitted from each of the plurality of detection ICs 13 via the signal pattern 15, and transfers the received digital data to the monitoring device 200.

Figure 6:
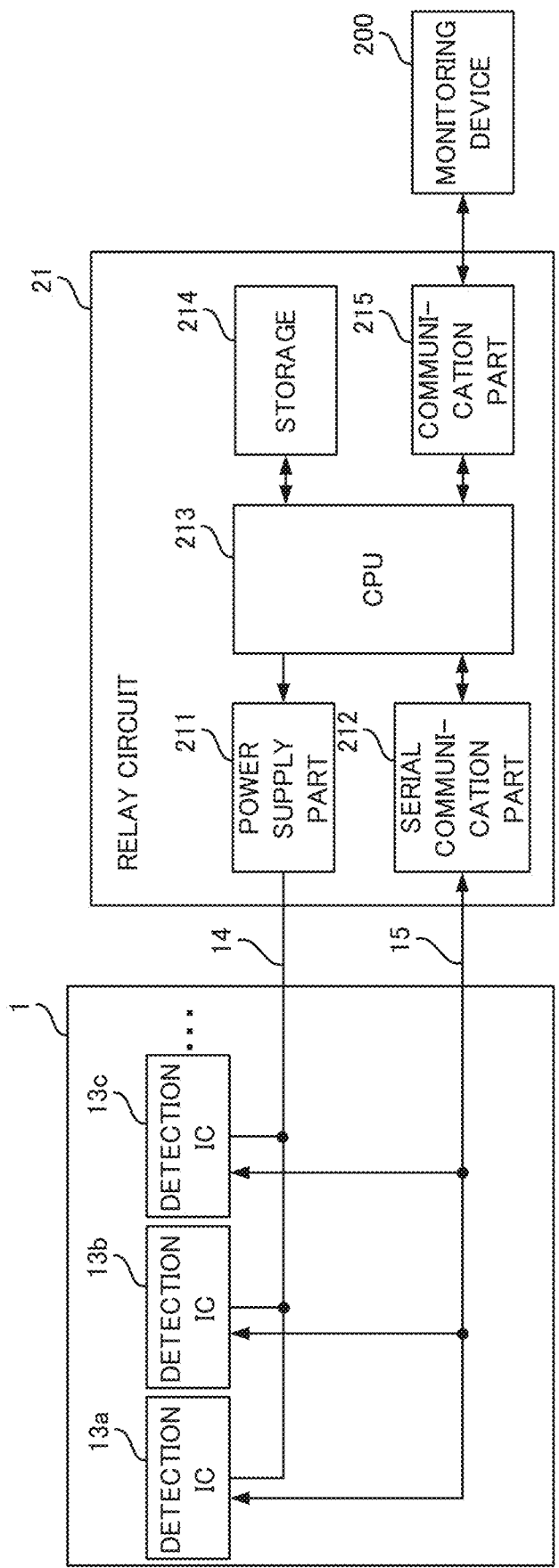
FIG. 6 shows a configuration of a relay circuit.

FIG. 6 shows a configuration of the relay circuit 21. The relay circuit 21 includes a power supply part 211, a serial communication part 212, a CPU 213, a storage 214, and a communication part 215.

The power supply part 211 generates power for operating the plurality of detection ICs 13 and starts supplying the power to the plurality of detection ICs 13 on the basis of the control of the CPU 213.

The serial communication part 212 has a communication controller to transmit and receive digital data in a time-division multiplexing manner between the plurality of detection ICs 13 in a format determined by, for example, a communication method such as SPI or I2C. The serial communication part 212 transmits the control data for controlling each of the plurality of detection ICs 13. Further, the serial communication part 212 receives the digital data indicating the voltage value detected by each of the plurality of detection ICs 13. The serial communication part 212 notifies the CPU 213 of the digital data received from the detection IC 13 in association with identification information for identifying each of the detection ICs 13.

The CPU 213 temporarily stores in the communication part 215 the digital data received from the detection IC 13 via the serial communication part 212. The CPU 213 transmits the temporarily stored digital data to the monitoring device 200 via the communication part 215.

The storage 214 includes, for example, a ROM and a RAM, and stores the digital data from the detection IC 13 received by the CPU 213. Further, the storage 214 also stores a program to be executed by the CPU 213.

The communication part 215 transmits the digital data stored in the storage 214 to the monitoring device 200 on the basis of an instruction from the CPU 213. Moreover, the communication part 215 receives the control data from the monitoring device 200 and notifies the CPU 213 of the received control data. The communication part 215 transmits and receives data to and from the monitoring device 200 via, for example, a Universal Serial Bus (USB). The communication part 215 may transmit and receive data to and from the monitoring device 200 via a wireless channel such as Bluetooth (registered trademark). In addition, the monitoring device 200 may transmit measurement data to a data storage and analysis device such as a cloud server through a portable communication network or the like.

[Variations of a Shape of an Electrode]
(First Variation)

Figure 7:
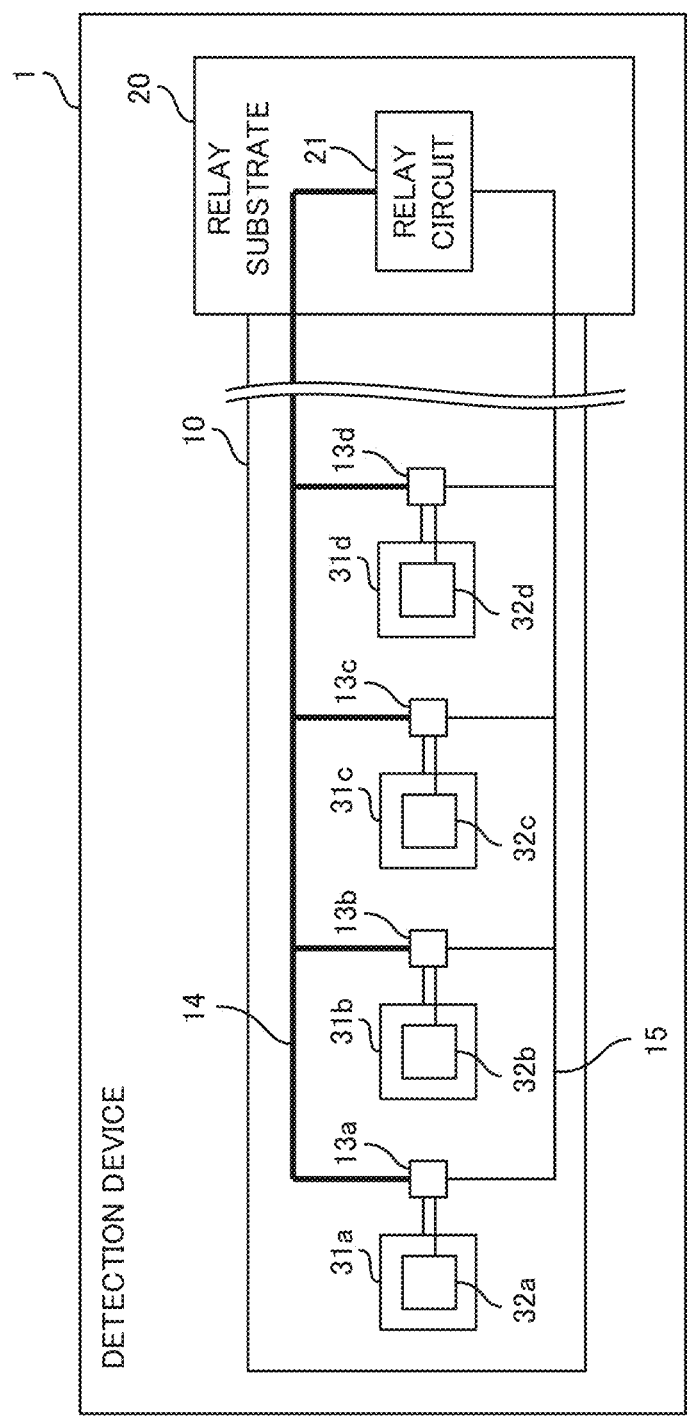
FIG. 7 shows a configuration of a first variation of an electrode.

FIG. 7 shows a configuration of a first variation of an electrode. The detection device 1 shown in FIG. 7 has a positive electrode 31 and a negative electrode 32 instead of the positive electrode 11 and the negative electrode 12 shown in FIG. 3. The negative electrode 32 is surrounded by the positive electrode 31. Specifically, the negative electrode 32 is smaller than the positive electrode 31, and the positive electrode 31 and the negative electrode 32 are provided on the flexible substrate 10 so that a projection surface of the negative electrode 32 in the thickness direction of the flexible substrate 10 is included in a region surrounded by the contour of the positive electrode 31.

Figure 8A:
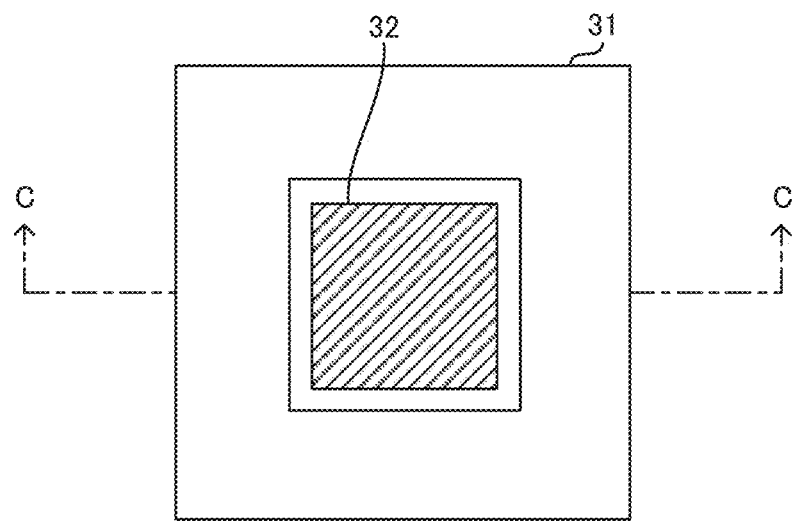
FIGS. 8A and 8B each show detailed configurations of the positive electrode and the negative electrode.
Figure 8B:

FIGS. 8A and 8B each show detailed configurations of the positive electrode 31 and the negative electrode 32. FIG. 8A is a plane figure of the positive electrode 31 and the negative electrode 32, and FIG. 8B is a B-B-line cross section thereof. The positive electrode 31 shown in FIG. 8 has a square contour and has a square void region capable of accommodating the negative electrode 32 therein, but the contour shape and the shape of the void region inside of the positive electrode 31 are arbitrary.

Figure 9:
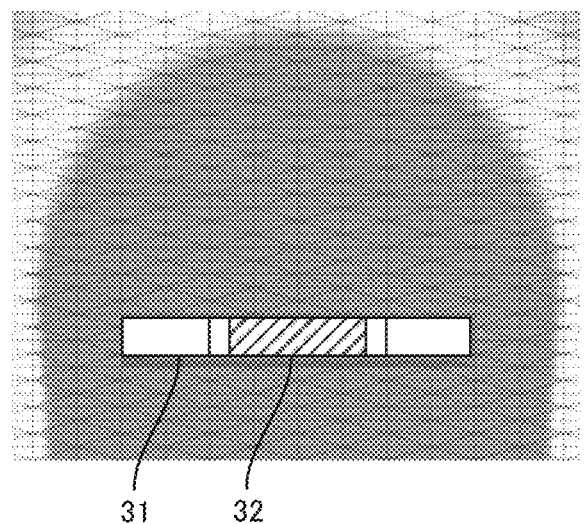
FIG. 9 shows a current density distribution generated around the positive electrode and the negative electrode.

FIG. 9 shows a current density distribution generated around the positive electrode 31 and the negative electrode 32. The current density distribution is proportional to the intensity distribution of the electric field generated around the positive electrode 31 and the negative electrode 32. In FIG. 9, the current density in the dark-colored region is greater than the current density in the light-colored region. It can be seen that the strong electric field region occurs between the positive electrode 31 and the negative electrode 32 due to the electric field generator 131 supplying the weak current to the positive electrode 31. Since the positive electrode 31 and the negative electrode 32 are configured as shown in FIG. 7, it is possible to detect a change in the electric field in a narrower area than the configuration shown in FIG. 3. The positional relationship between the positive electrode 31 and the negative electrode 32 may be reversed, that is, the negative electrode 32 may surround the positive electrode 31.

Figure 10:
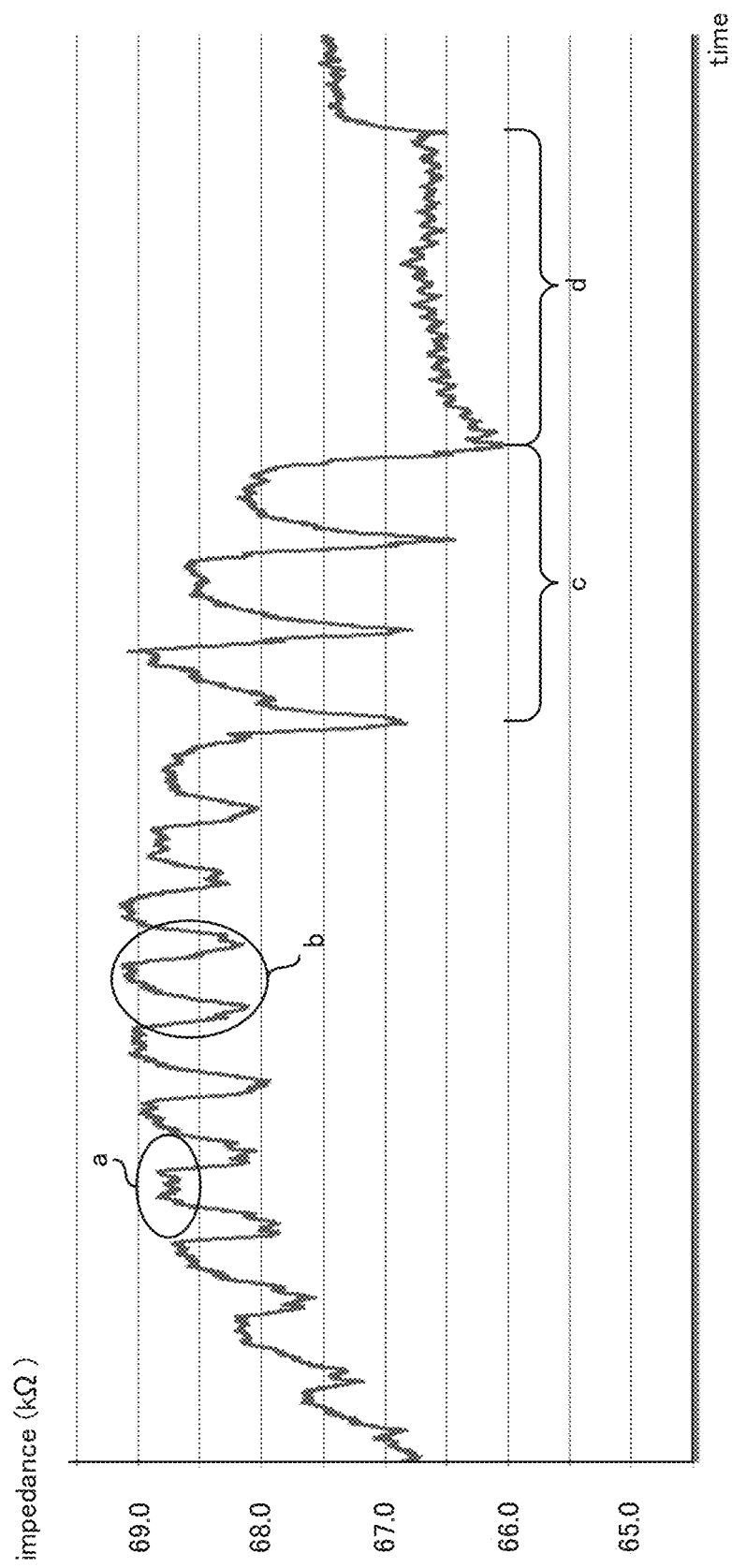
FIG. 10 shows a change in impedance between the positive electrode and the negative electrode when the positive electrode and the negative electrode are attached to a person's chest.

FIG. 10 shows the change in the impedance between the positive electrode 31 and the negative electrode 32 when the positive electrode 31 and the negative electrode 32 shown in FIG. 8 are mounted on a person's chest. With the positive electrode 31 and the negative electrode 32 attached to clothes on the person's chest, the potential difference between the positive electrode 31 and the negative electrode 32 occurring while a weak current having a frequency of 1 MHz was flowing through the positive electrode 31 was measured. Then, the impedance was calculated on the basis of i) the magnitude of the weak current (current value) flowing through the positive electrode 31 and the negative electrode 32 and ii) the measured potential difference. The contour shape of the positive electrode 31 used was a square having a side of 40 mm.

FIG. 10 shows the change in the impedance in synchronization with the heartbeat (a in FIG. 10) and the change in the impedance in synchronization with the breathing (b in FIG. 10). It can also be confirmed that the amount of the change in the impedance increases when the person takes a deep breath (c in FIG. 10), and the amount of the change in the impedance decreases while the person holds his/her breath (d in FIG. 10).

It should be noted that, in the embodiment shown in FIG. 7, the detection IC 13 is provided at a position adjoining the corresponding positive electrode 31 along the longitudinal direction of the seat belt 100, but the detection IC 13 may be provided at other positions. The detection IC 13 may be provided at a position adjoining the positive electrode 31 corresponding to the detection IC 13 in the transverse direction of the seat belt 100, for example. The detection IC 13 may be provided on a rear surface of the positive electrode 31 or the negative electrode 32 via a shielding surface or the like. Providing the detection ICs 13 at such positions enables the positive electrodes 31 to be arranged at high density, and so the resolution of the detection device 1 can be increased.

(Second Variation)

Figure 11A:
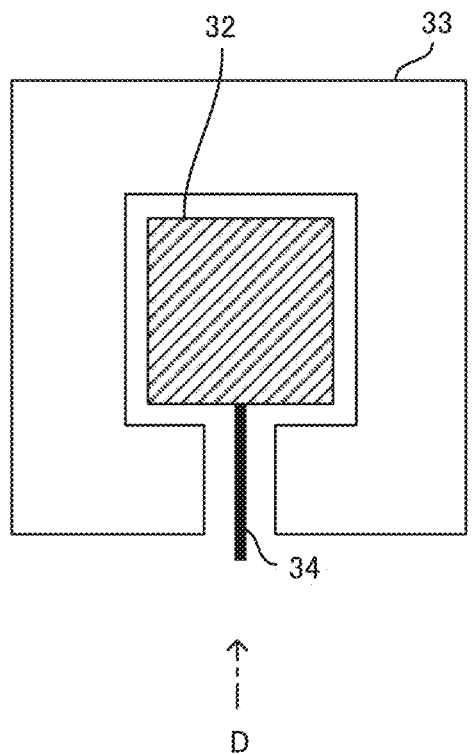
FIGS. 11A and 11B each show a configuration of a second variation of an electrode.
Figure 11B:
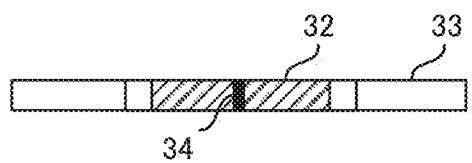

FIGS. 11A and 11B each show a configuration of a second variation of the electrode. FIG. 11A is a plane figure of a positive electrode 33 and the negative electrode 32 according to the present variation, and FIG. 11B is the positive electrode 33 and the negative electrode 32 viewed from the direction D. The positive electrode 33 surrounds the negative electrode 32 in a region excluding a position where wiring 34 for connecting the negative electrode 32 and the detection IC 13 is provided. The positive electrode 33 is not provided at a position where the wiring 34 is provided, and so the wiring 34 does not overlap the positive electrode 33. If the wiring 34 and the positive electrode 33 overlap, an electric field occurs in a region where the wiring 34 and the positive electrode 33 overlap, which leads to the loss of energy. Since the negative electrode 32 and the positive electrode 33 are configured as shown in FIG. 11, the detection device 1 can suppress the loss of energy, and so the measurement accuracy of the potential difference between the negative electrode 32 and the positive electrode 33 can be improved.

(Third Variation)

Figure 12A:
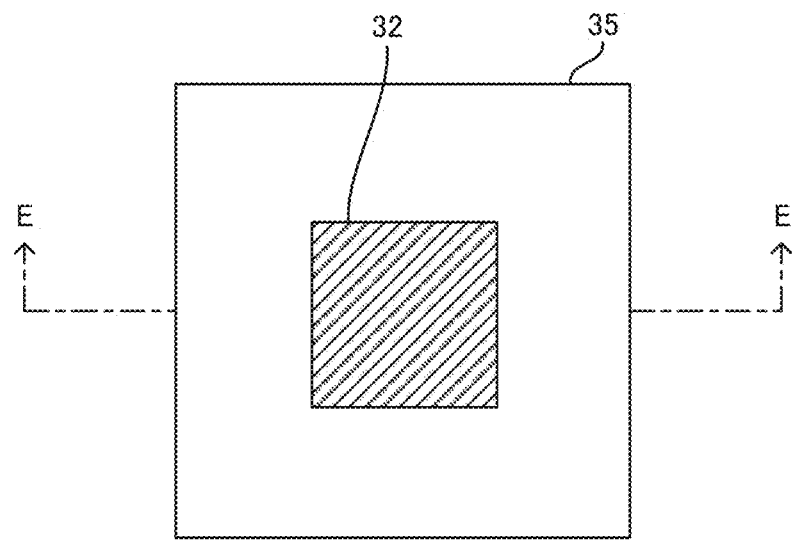
FIGS. 12A and 12B each show a configuration of a third variation of an electrode.
Figure 12B:
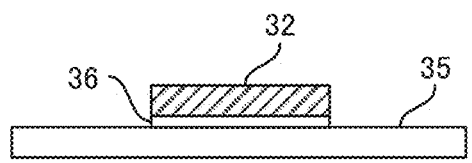

FIGS. 12A and 12B each show a configuration of a third variation of the electrode. FIG. 12A is a plane figure of a positive electrode 35 and the negative electrode 32 according to the present variation, and FIG. 12B is an E-E-line cross section thereof. The positive electrode 35 has a square shape, and the negative electrode 32 is provided above the positive electrode 35 with an insulating member 36 interposed therebetween. Even with such a configuration, an electric field equivalent to that of the positive electrode 31 and the negative electrode 32 shown in FIG. 8 can be generated.

[A Guard Electrode]

The detection device 1 may further include a guard electrode provided on a surface of the flexible substrate 10 opposite to a surface on which the positive electrode and the negative electrode are provided. In this case, the detection IC 13 includes a potential adjustment circuit for making the potential of the guard electrode the same as that of the negative electrode.

Figure 13A:
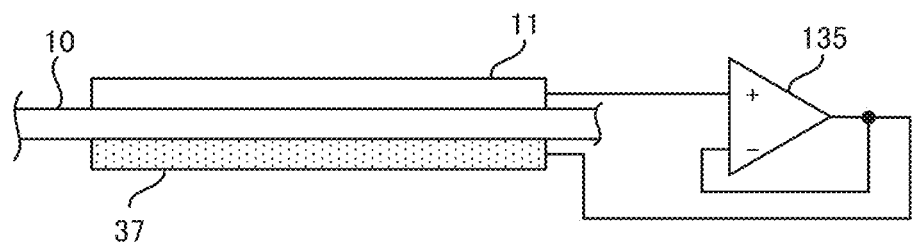
FIGS. 13A, 13B, and 13C each show a configuration example in which a guard electrode is provided.
Figure 13B:
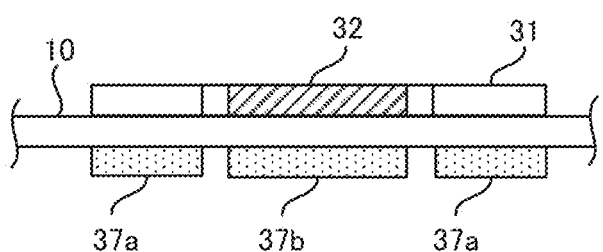
Figure 13C:
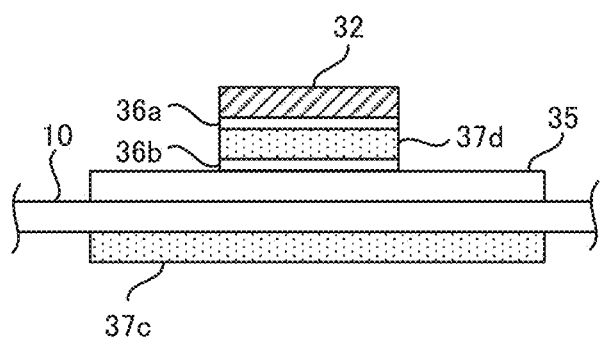

FIGS. 13A, 13B, and 13C each show a configuration example in which the guard electrode is provided. FIG. 13A shows an example of the electrode pair E in which a guard electrode 37 is provided on the surface of the flexible substrate 10 shown in FIGS. 3A and 3B opposite to a surface on which the positive electrode 11 is provided. The guard electrode 37 is connected to the potential adjustment circuit including an operational amplifier 135.

The potential adjustment circuit in the example shown in FIG. 13A is a voltage follower. The positive electrode 11 is connected to a positive input terminal of the operational amplifier 135, and the guard electrode 37 is connected to an output terminal of the operational amplifier 135, and so the potential of the guard electrode 37 is equal to the potential of the positive electrode 11. Although not shown in FIG. 13A, the detection device 1 may further include a guard electrode provided on the surface of the flexible substrate 10 opposite to a surface on which the negative electrode 12 is provided, and a potential adjustment circuit for equalizing the potential of the guard electrode with the potential of the negative electrode 12.

FIG. 13B shows an example in which a guard electrode 37a and a guard electrode 37b are each provided on the surface of the flexible substrate 10 opposite to a surface on which the positive electrode 31 and the negative electrode 32 shown in FIG. 8 are provided. FIG. 13C shows an example in which a guard electrode 37c is provided on the surface of the flexible substrate 10 opposite to the surface on which the positive electrode 35 shown in FIG. 12 is provided. In the example shown in FIG. 13C, a guard electrode 37d is provided between the positive electrode 35 and the negative electrode 32 via the insulator 36a and the insulator 36b.

Although not shown in FIGS. 13B and 13C, the detection device 1 may include i) a potential adjustment circuit for equalizing the potential of the guard electrode 37a with the potential of the positive electrode 31, ii) a potential adjustment circuit for equalizing the potential of the guard electrode 37b with the potential of the negative electrode 32, and iii) a potential adjustment circuit for equalizing the potential of the guard electrode 37c with the potential of the positive electrode 35. Since the guard electrode and the potential adjustment circuit are provided in the detection device 1 in this manner, the electric field generated by the current, flowing through the positive electrode 11, the positive electrode 31, or the positive electrode 35, does not leak to the opposite surface of the flexible substrate 10, and so the electric field intensity on the surface on which the positive electrode 11, the positive electrode 31, or the positive electrode 35 is provided is increased. As a result, the monitoring system S can improve the accuracy in detecting the movement amount of the human body.

It should be noted that the shape of the electrode is not limited to a square or a rectangle, and may be a circle, an ellipse, or a polygon other than a square or a rectangle. Further, a shield layer (ground potential layer) may be provided on a rear surface of at least one of the positive electrode 31, the negative electrode 32, and the guard electrode 37.

Furthermore, if the shield layer is provided, an insulating member may be provided below the guard electrode 37 (that is, a surface of the guard electrode 37 opposite to the surface facing the flexible substrate 10) to provide the shield layer below the insulating member. That is, in this case, the insulating member is provided between the guard electrode 37 and the shield layer. With such a configuration, the electric field intensity on the surface on which the positive electrode 11, the positive electrode 31, or the positive electrode 35 is provided is further increased.

[Control of an Electric Field Generated Region]

The monitoring system S can control the region where the electric field is generated by controlling which electrode the current flows through, among the plurality of electrodes provided in the detection device 1. More specifically, the CPU 213 functions as a controller that controls the plurality of detection ICs 13 to acquire the electric field intensity detection value corresponding to the intensity of an electric field generated between one positive electrode selected from a plurality of positive electrodes and one negative electrode selected from a plurality of negative electrodes, for example, on the basis of an instruction from the monitoring device 200. The plurality of detection ICs 13 outputs the electric field intensity detection value corresponding to the intensity of the electric field generated between any of the plurality of positive electrodes and any of the plurality of negative electrodes.

Figure 14A:
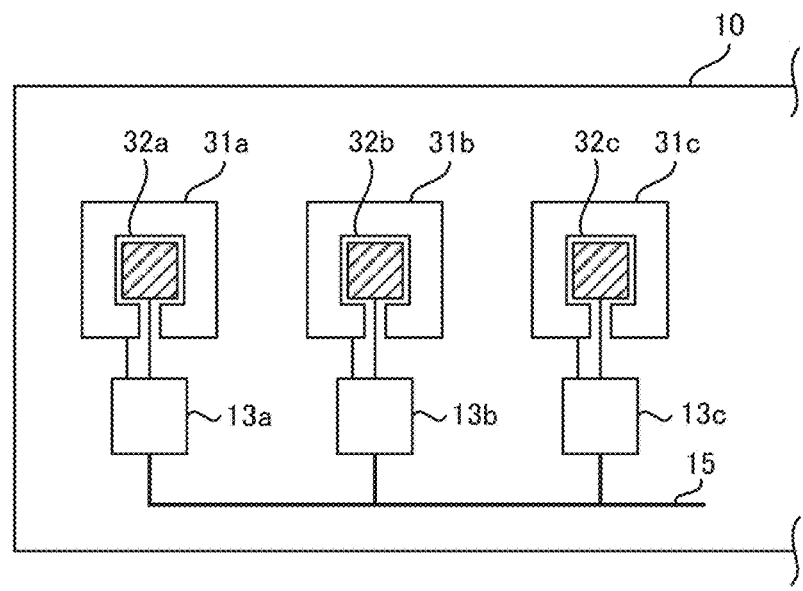
FIGS. 14A, 14B, and 14C are each a figure for explaining a method for controlling a region where a CPU generates an electric field.
Figure 14B:
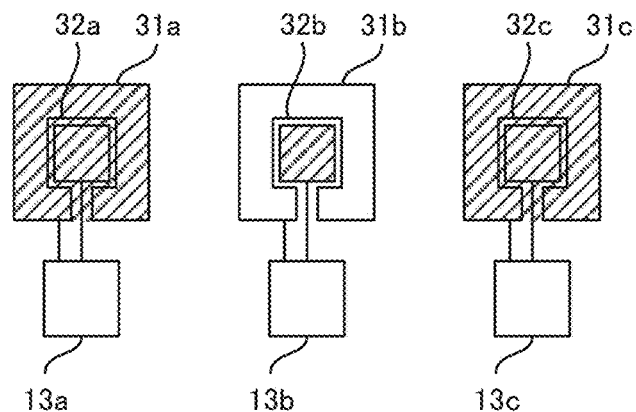
Figure 14C:
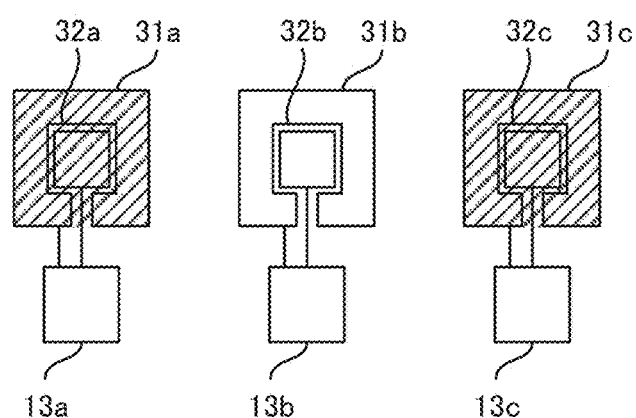

FIGS. 14A, 14B, and 14C are each a figure for explaining a method for controlling the region where the CPU 213 generates the electric field. In FIGS. 14A, 14B, and 14C, the weak current flows in blank regions of the positive electrode 31a, the positive electrode 31b, and the positive electrode 31c, and hatched regions of the positive electrode 31a, the positive electrode 31b, and the positive electrode 31c are set to have the ground potential and to have no weak current flowing therein. In the state shown in FIG. 14A, since the weak current flows through each of the positive electrode 31a, the positive electrode 31b, and the positive electrode 31c, the electric field shown in FIG. 9 is generated each of between the positive electrode 31a and the negative electrode 32a, between the positive electrode 31b and the negative electrode 32b, and between the positive electrode 31c and the negative electrode 32c.

In contrast, in the state shown in FIG. 14B, no weak current flows from the positive electrode 31a and the positive electrode 31c. Therefore, an electric field is generated between the positive electrode 31b and the negative electrode 32b, between the positive electrode 31b and the positive electrode 31a, and between the positive electrode 31b and the positive electrode 31c. Consequently, the electric field differing from the state shown in FIG. 14A is generated.

In the state shown in FIG. 14C, current is controlled so that the same weak current flows through the positive electrode 31b and through the negative electrode 32b. In this state, the electric field occurs i) between a) the positive electrode 31b and the negative electrode 32b and b) the positive electrode 31a and the negative electrode 32a, and ii) between a) the positive electrode 31b and the negative electrode 32b and c) the positive electrode 31c and the negative electrode 32c. It should be noted that the ground potential in FIG. 14 may be a negative potential in an AC voltage.

In this way, each of the detection IC 13a, the detection IC 13b, and the detection IC 13c switches the electrode to which the current flows on the basis of the control signal received from the CPU 213, to change the region where the electric field is generated. Since the monitoring system S changes the region where the electric field is generated in this way to measure a movement state of the human body using various electric field generating states, the substantial measurement resolution can be improved.

[Detection of the Movement Amount by a Shape Sensor]

Figure 15:
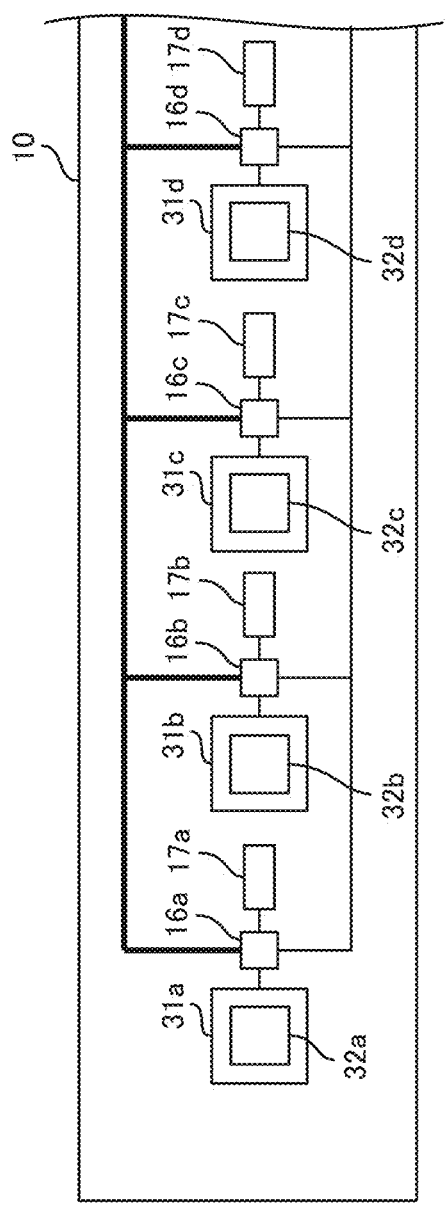
FIG. 15 shows another example of a flexible substrate according to the embodiment.

FIG. 15 shows another example of the flexible substrate 10 according to the embodiment. The flexible substrate 10 shown in FIG. 15 differs from the flexible substrate 10 shown in FIG. 7 in that it further includes a plurality of shape sensors 17 (a shape sensor 17a, a shape sensor 17b, a shape sensor 17c, and a shape sensor 17d). The shape sensor 17 includes a curvature sensor 171 (also referred to as a strain gauge) whose impedance changes according to a curvature of the flexible substrate 10 at the position where the shape sensor 17 is provided.

Figure 16A:
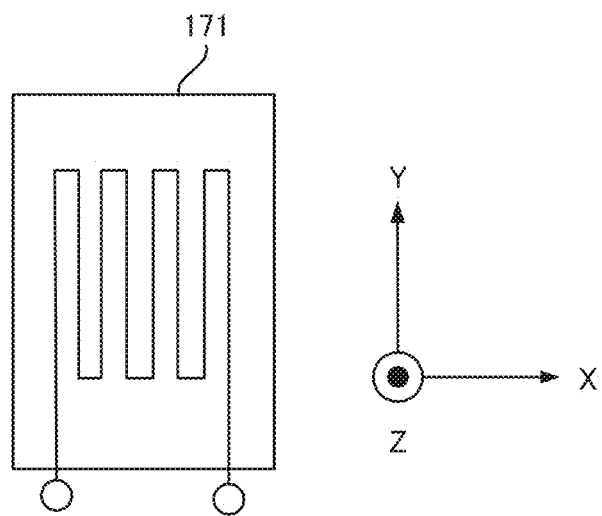
FIGS. 16A, 16B, and 16C each schematically show a shape of a curvature sensor.
Figure 16B:
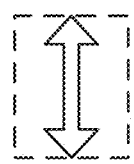
Figure 16C:
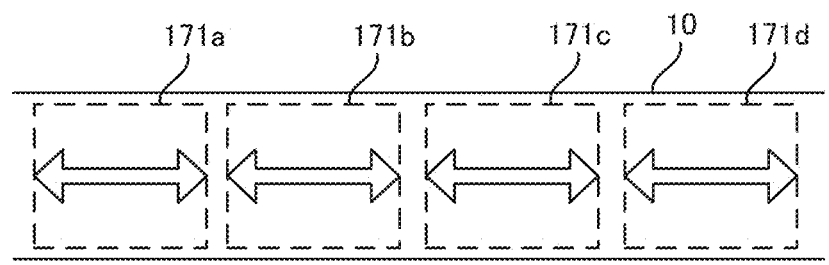

FIGS. 16A, 16B, and 16C each schematically show a shape of the curvature sensor 171. As shown in FIG. 16A, the curvature sensor 171 includes conductive wiring having a plurality of portions in the X-direction and a plurality of portions in the Y-direction. Said wiring has a comb shape in which the length of each portion in the Y-direction is larger than the length of each portion in the X-direction. When the curvature sensor 171 is bent so that its position in the Z-direction becomes different at different positions in the Y-direction, the impedance of the curvature sensor 171 changes due to the change in the distance between the plurality of wiring portions constituting the curvature sensor 171.

FIG. 16B is a symbol indicating the curvature sensor 171 shown in FIG. 16A. An arrow shown in FIG. 16B corresponds to the Y-direction in FIG. 16A, that is, the longitudinal direction of the wiring. FIG. 16C is a schematic figure showing a state in which a plurality of curvature sensors 171 are disposed on the flexible substrate 10. In the example shown in FIG. 16C, a curvature sensor 171a, a curvature sensor 171b, a curvature sensor 171c, and a curvature sensor 171d are arranged at equal intervals.

The flexible substrate 10 is provided with, instead of the detection IC 13 in FIG. 3, i) a circuit for detecting the potential difference by applying a constant voltage or a constant current to the circuit including the curvature sensor 171 and ii) a plurality of detection ICs 16 each having a circuit for detecting the potential difference caused by the impedance change of respective ones of the plurality of shape sensors 17. Each of the plurality of detection ICs 16 transmits digital data indicating the impedance to the relay substrate 20 via the same serial signal line.

Figure 17:
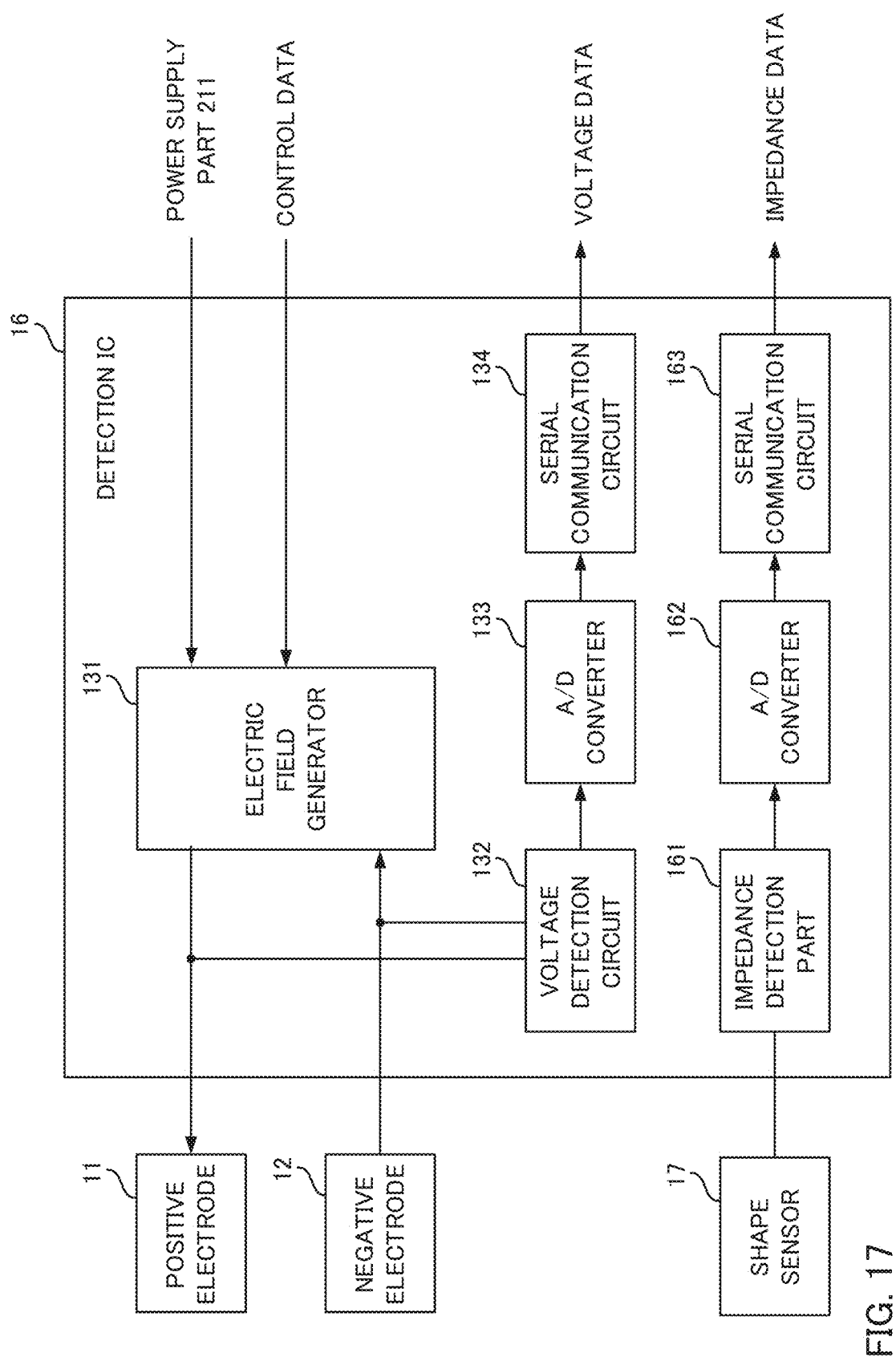
FIG. 17 shows a configuration of a detection IC.

FIG. 17 shows a configuration of the detection IC 16. The detection IC 16 includes an impedance detection part 161, an A/D converter 162, and a serial communication circuit 163, in addition to the electric field generator 131, the voltage detection circuit 132, the A/D converter 133, and the serial communication circuit 134 included in the detection IC 13.

The impedance detection part 161 detects the impedance of the curvature sensor 171. Specifically, the impedance detection part 161 calculates the impedance of the curvature sensor 171, and inputs the calculated impedance to the A/D converter 162. The A/D converter 162 converts an analog signal corresponding to the inputted impedance into digital data, and inputs the digital data to the serial communication circuit 163. The serial communication circuit 163 has the same function as the serial communication circuit 134, and transmits the digital data (impedance data) via a serial communication line, such as SPI or I2C, as digital data inputted from the A/D converter 162.

Thus, in a case where the detection device 1 includes the shape sensor 17, the monitoring device 200 identifies the state of the driver's body on the basis of the electric field intensity detection value outputted by the detection IC 16 and the impedance of the curvature sensor 171 outputted by the detection IC 16. Since the shape of the chest slightly changes due to the breathing or the heartbeat, it is suitable to identify the state of the driver's body on the basis of the change in the curvature of the shape sensor 17 when there is a possibility of being affected by the change in electric field caused by external electrical equipment and the like. The detection sensitivity of the method for identifying the state of the driver's body by the change in the curvature of the shape sensor 17 is often lower than that of the electric field intensity detection method. However, it is expected to be advantageous when there are concerns about adverse effects due to application of the electric field, for example, for a person who wears a pacemaker.

The monitoring device 200 may be made not to use the electric field intensity detection value and the impedance for identifying the state of the body if the plurality of states of the body respectively identified on the basis of the electric field intensity detection value and the impedance simultaneously acquired by the detection device 1 do not match. In order to improve the safety of vehicle travel, the monitoring device 200 may determine that the vehicle needs to be stopped if the plurality of states of the body does not match with each other or if one of them indicates an abnormality in the state of the body.

It should be noted that FIG. 17 shows an example in which the detection IC 16 includes the serial communication circuit 134 and the serial communication circuit 163, but the detection IC 16 does not have to include the serial communication circuit 163, and the A/D converter 162 may input the digital data indicating the impedance to the serial communication circuit 134. In this case, the serial communication circuit 134 transmits digital data generated by multiplexing the digital data indicating the potential difference inputted from the A/D converter 133 and the digital data indicating the impedance inputted from the A/D converter 162.

In order to enable the monitoring device 200 to identify i) the potential difference between the positive electrode 11 and the negative electrode 12 detected simultaneously and ii) the impedance of the shape sensor 17, the A/D converter 133 and the A/D converter 162 may acquire i) the analog signal indicating the potential difference and ii) the analog signal indicating the impedance, on the basis of the same sampling clock. Further, the serial communication circuit 134 may transmit i) the digital data indicating the potential difference simultaneously sampled at the change point of the sampling clock and ii) the digital data indicating the impedance, in association with each other. The serial communication circuit 134 transmits, for example, the digital data indicating the potential difference and the digital data indicating the impedance as consecutive two-byte data.

Figure 18A:
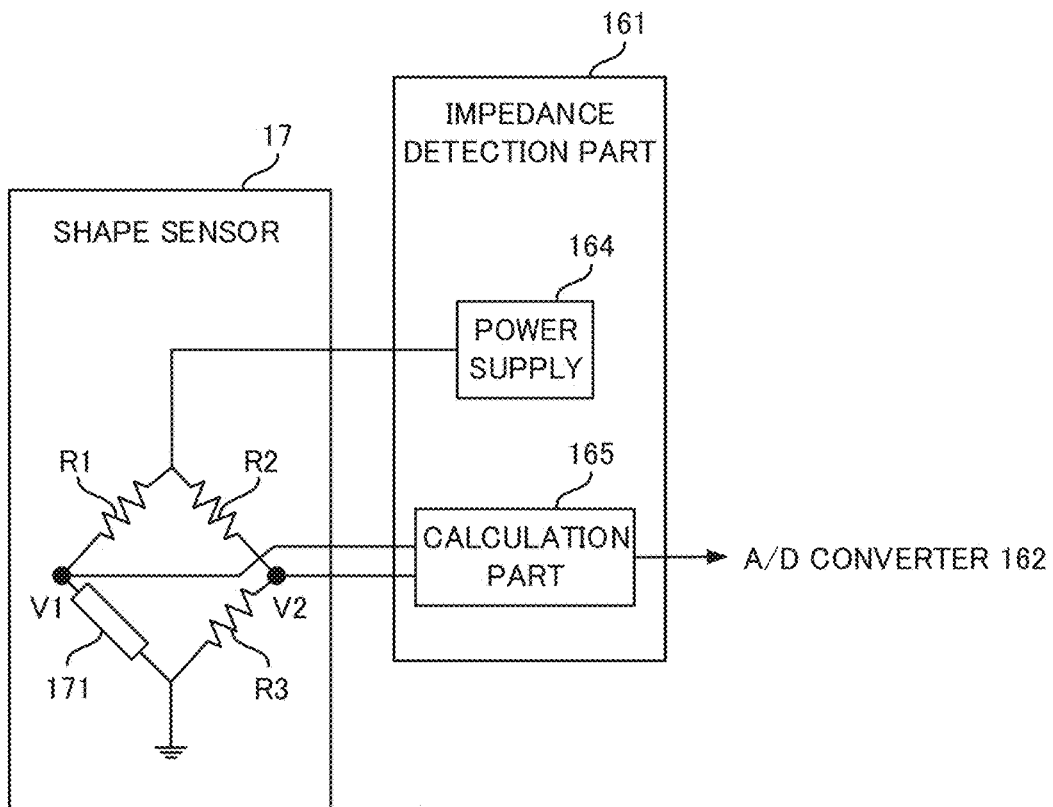
FIGS. 18A and 18B each show configurations of a shape sensor and an impedance detection part.
Figure 18B:
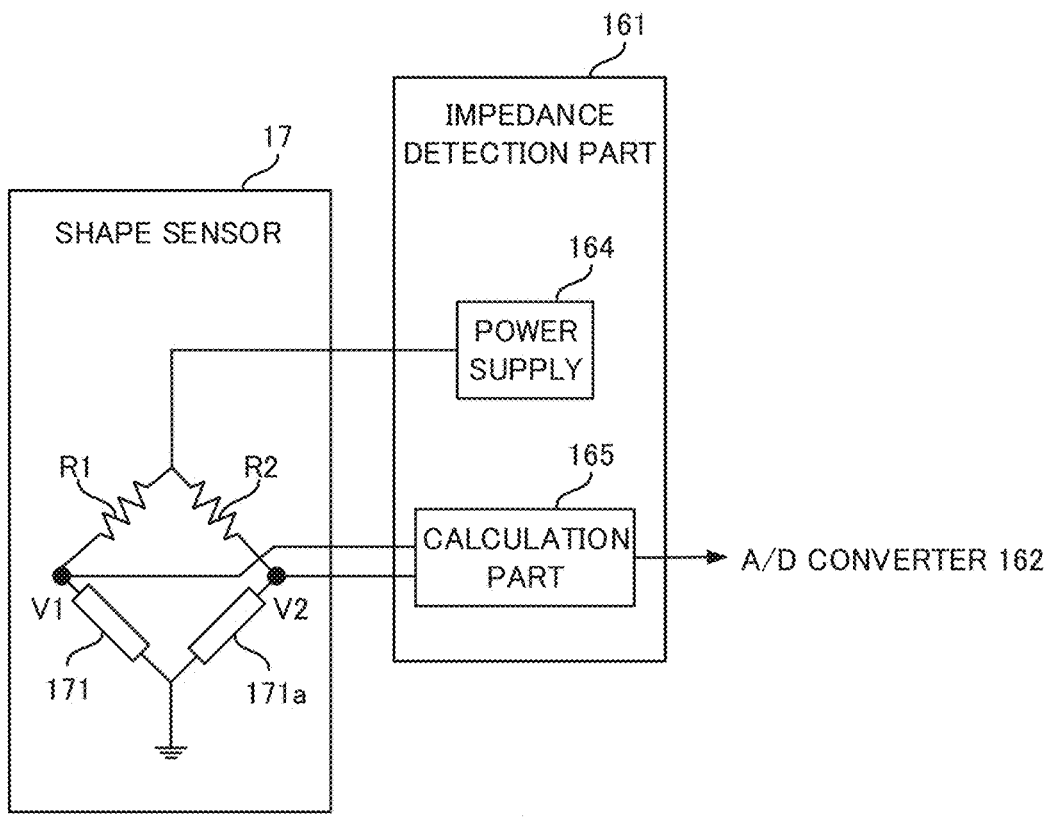

FIGS. 18A and 18B each show configurations of the shape sensor 17 and the impedance detection part 161. The impedance detection part 161 includes a power supply 164 and a calculation part 165. The power supply 164 functions as a power supply for supplying power to the shape sensor 17. In the example shown in FIG. 18A, the shape sensor 17 includes a resistor R1 connected in parallel with the curvature sensor 171 between the power supply and the reference potential, and a resistor R2 and a resistor R3 provided in parallel with the resistor R1 and the curvature sensor 171. The calculation part 165 acquires, in a state where the power is supplied to the shape sensor 17, a first potential V1 between the resistor R1 and the curvature sensor 171 and a second potential V2 between the resistor R2 and the resistor R3, and calculates the impedance of the curvature sensor 171 on the basis of the obtained first potential V1 and second potential V2.

When the voltage supplied by the power supply 164 is Vcc and the impedance of the curvature sensor 171 is Z1, the relationship shown in the following equation (1) is established.

$$V1-V2=Vcc\times((Z1/(R1+Z1))-(R3/(R2+R3))) \qquad (1)$$

If Vcc, R1, R2, and R3 are known, the calculation part 165 can calculate the impedance of the curvature sensor 171 by using this relationship shown in equation (1).

In the example shown in FIG. 18B, the shape sensor 17 has a curvature sensor 171a instead of R3 in FIG. 18A. The curvature sensor 171a is provided, for example, on the surface of the flexible substrate 10 opposite to a surface on which the curvature sensor 171 is provided. In this case, when the impedance of the curvature sensor 171a is Z2, the relationship shown in the following equation (2) is established.

$$V1-V2=Vcc\times((Z1/(R1+Z))-(Z2/(R2+Z2))) \qquad (2)$$

When the curvature sensor 171 and the curvature sensor 171a are provided such that they each bend to opposite sides with the same curvature, $\Delta Z1=-\Delta Z2$ is established, where $\Delta Z1$ is the amount of change in the impedance Z1 in the curvature sensor 171 and $\Delta Z2$ is the amount of change in the impedance Z2 in the curvature sensor 171a. When R1=R2=R is known and the initial Z1 is known to be Z1=Z2, the potential difference after bending the curvature sensor 171 by a certain amount is expressed by the following equation (3) by substituting them into the above equation (2).

$$V1-V2=Vcc\times(((Z1+\Delta Z1)/(R+(Z1+\Delta Z1)))-((Z1-\Delta Z1)/(R+(Z1-\Delta Z1)))) \qquad (3)$$

On the other hand, equation (1) can be modified as follows.

$$V1-V2=Vcc\times(((Z1+\Delta Z1)/(R1+(Z1+\Delta Z)))-(R3/(R2+R3))) \qquad (4)$$

Figure 19:
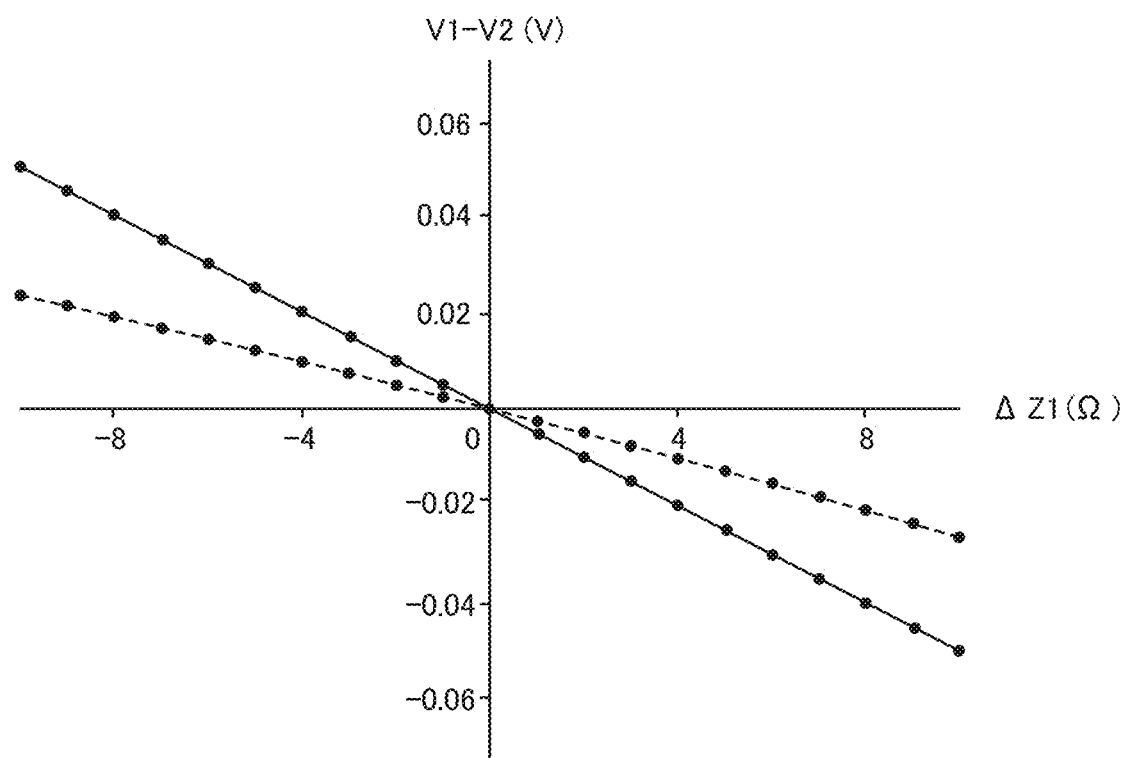
FIG. 19 shows a relation of the potential difference V1–V2 with respect to the change amount of ΔZ1.

Here, a relation of the potential difference V1−V2 with respect to the change amount of $\Delta Z1$ when $\Delta Z1$ varies by 1% at a time in a range of ±10% was simulated, using Vcc=1V, R1=100Ω, R2=100Ω, R3=100Ω, Z1=1000 (reference value), and Z2=Z1=100Ω (reference value). FIG. 19 shows the relation of the potential difference V1−V2 with respect to the change amount of $\Delta Z1$. A solid line in FIG. 19 shows the case where the curvature sensor 171 and the curvature sensor 171a are used, and a broken line shows the case where only the curvature sensor 171 is used.

Compared to equation (4) in which only the curvature sensor 171 is used, equation (3) in which the curvature sensor 171 and the curvature sensor 171a are used shows that the change amount of the potential difference V1−V2 with respect to the change amount of $\Delta Z1$ is doubled. That is, the impedance change amount $\Delta Z1$ can be measured and calculated as a doubled change amount.

Further, when the curvature sensor 171 and the curvature sensor 171a are provided on both surfaces of the flexible substrate 10 and R1=R2, the impedance change amount according to the temperature is $\Delta Z1=\Delta Z2$ even if Z1 and Z2 are changed according to the temperature. In this instance, (Z1/(R1+Z1))−(Z2/(R2+Z2)) in the above equation (2) is approximately constant. Therefore, the calculation part 165 can calculate the impedance changes of the curvature sensor 171 and the curvature sensor 171a with a high sensitivity by compensating for the effect of the temperature change.

Figure 20A:
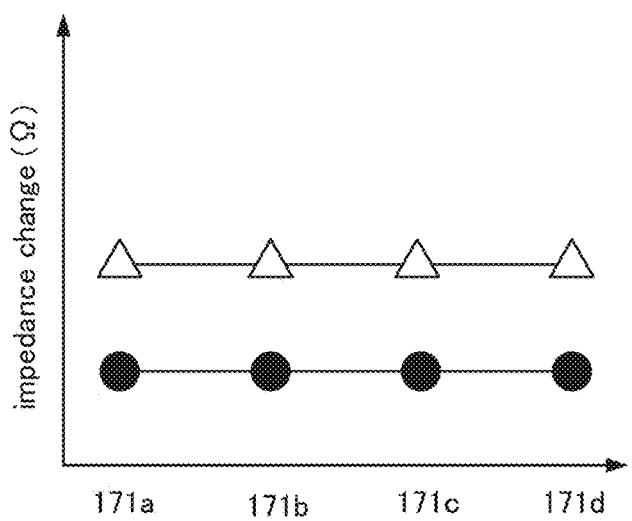
FIGS. 20A, 20B, and 20C each show a relation between the impedance of the curvature sensor and a shape of the flexible substrate.
Figure 20B:
Figure 20C:
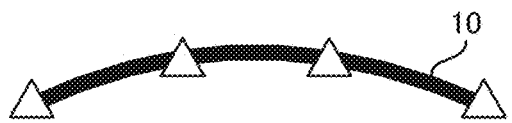

FIGS. 20A, 20B, and 20C each show the relation between the impedance of the curvature sensor 171 and the shape of the flexible substrate 10. In FIG. 20A, the horizontal axis shows the position of each of the plurality of curvature sensors 171, and the vertical axis indicates the impedance. Black dots (○) in FIG. 20A show the impedance when the curvature sensor 171 is not deformed. White triangles (△) in FIG. 20A show the impedance of each curvature sensor 171 when deformed at the same curvature.

FIG. 20B is a schematic diagram of the shape of the flexible substrate 10 when the plurality of curvature sensors 171 has an impedance indicated by ○ in FIG. 20A. FIG. 20C is a schematic diagram of the shape of the flexible substrate 10 when the plurality of curvature sensors 171 has the impedance indicated by A in FIG. 20A. The monitoring device 200 uses such a relationship between the impedance and the curvature to identify the shape of the flexible substrate 10 on the basis of the impedance value of each of the plurality of curvature sensors 171 received via the relay circuit 21.

It should be noted that each of the plurality of detection ICs 16 may execute a) the detection process of the intensity of the electric field generated between the positive electrode and the negative electrode (in the example of FIG. 17, the positive electrode 11 and the negative electrode 12) and b) the detection process of the impedance, while switching in a time-division manner. Specifically, while the detection IC 16 is generating the electric field between the positive electrode and the negative electrode, the impedance detection part 161 does not measure the impedance of the curvature sensor 171, and the voltage detection circuit 132 measures the potential difference between the positive electrode and the negative electrode. While the detection IC 16 is not generating the electric field between the positive electrode and the negative electrode, the voltage detection circuit 132 does not measure the potential difference, and the impedance detection part 161 measures the impedance of the curvature sensor 171. As described above, the detection IC 16 executes the detection process of the electric field intensity and the detection process of the impedances in a time-division manner, and so one of the detection processes is not electrically affected while the other detection process is performed, which improves the measuring accuracy.

[A Variation of Directions of the Plurality of Curvature Sensors 171]

Figure 21:
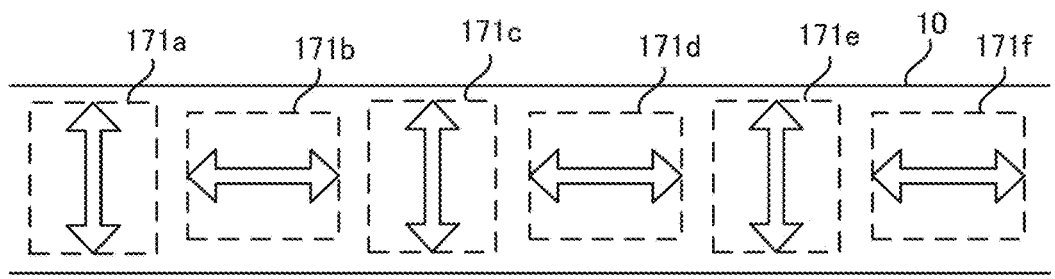
FIG. 21 shows a variation of directions of the plurality of curvature sensors.

FIG. 21 shows a variation of directions of the plurality of curvature sensors 171. The detection device 1 shown in FIG. 21 includes the plurality of curvature sensors 171 provided in different directions respectively at different positions along the longitudinal direction of the flexible substrate 10. Specifically, in the flexible substrate 10 shown in FIG. 21, a) curvature sensors 171 whose longitudinal directions, the Y-direction, correspond to the transverse direction of the flexible substrate 10 and b) curvature sensors 171 whose Y-directions correspond to the longitudinal direction of the flexible substrate 10 are arranged one by one in order. More specifically, the curvature sensor 171a, the curvature sensor 171c, and the curvature sensor 171e are provided so that their Y-directions correspond to the transverse direction of the flexible substrate 10, and the curvature sensor 171b, the curvature sensor 171d, and the curvature sensor 171f are provided so that their Y-directions correspond to the longitudinal direction of the flexible substrate 10.

The impedance of the curvature sensor 171a, the curvature sensor 171c, and the curvature sensor 171e changes due to the deformation of the flexible substrate 10 in the of the flexible substrate 10, and the impedance of the curvature sensor 171b, the curvature sensor 171d, and the curvature sensor 171f changes due to the deformation of the flexible substrate 10 in the longitudinal direction of the flexible substrate 10. Therefore, the monitoring device 200 can identify a variety of deformation states in respective positions where the plurality of curvature sensors 171 is provided on the basis of the impedance of each of the plurality of curvature sensors 171.

[A Variation of a Mounting Position of the Curvature Sensor 171]

Figure 22A:
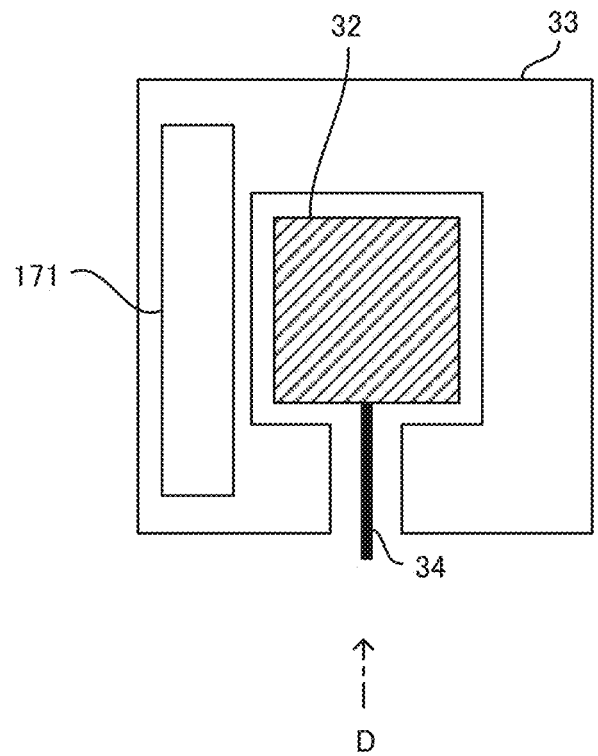
FIGS. 22A and 22B each show a configuration of a variation of mounting positions of the curvature sensors.
Figure 22B:
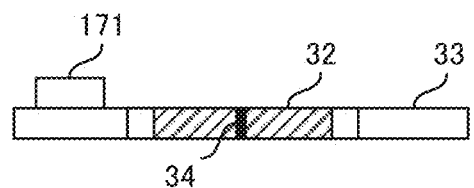

In the above description, the case where the curvature sensor 171 is directly mounted on the flexible substrate 10 is illustrated, but the curvature sensor 171 may be mounted on either the positive electrode or the negative electrode. FIGS. 22A and 22B each show a configuration of a variation of mounting positions of the curvature sensors 171. In FIGS. 22A and 22B, the curvature sensors 171 are mounted on the positive electrode 33. The curvature sensors 171 being mounted on either the positive electrode or the negative electrode in this way makes it possible to increase the mounting density of the electrode pairs and the curvature sensors 171, and so the measurement resolution is improved.

[Other Variations]

In the above, a case where the detection device 1 includes the relay substrate 20, and data is transmitted and received between the detection IC 13 and the relay substrate 20 by serial communication is illustrated, but the detection device 1 does not have to include the relay substrate 20. In this instance, the detection IC 13 directly transmits the electric field intensity detection value to the monitoring device 200 using the serial communication method such as SPI or I2C.

Further, in the above explanation, the detection device 1 includes the electrode pairs E and the detection ICs 13 on one surface of the flexible substrate 10, but the detection device 1 may include the electrode pairs E and the detection ICs 13 on both surfaces of the flexible substrate 10. In this case, the monitoring device 200 uses a plurality of electric field intensity detection values outputted by the plurality of detection ICs 13 corresponding to the plurality of electrode pairs E provided on both surfaces of the flexible substrate 10 at the same position along the longitudinal direction of the seat belt 100 to identify the electric field intensity at the same position. In this way, the monitoring device 200 can appropriately identify the state of the driver, even when the driver wears the seat belt 100 facedown.

If the electrode pairs E and the detection ICs 13 are provided on both surfaces of the flexible substrate 10, the monitoring device 200 may, for example, remove the common mode noise component contained in i) the electric field intensity detection value outputted by the detection IC 13 provided on the surface close to the driver and ii) the electric field intensity detection value outputted by the detection IC 13 on the other surface. The above configuration can reduce influence of the noise, and so the monitoring device 200 can improve the accuracy of identifying the state of the driver.

[Effect of the Detection Device 1]

As described above, the detection device 1 includes i) the electric field generator 131 for generating the electric field between the positive electrode and the negative electrode, and ii) the detection IC 13, provided on the flexible substrate 10, for outputting the electric field intensity detection value corresponding to the intensity of the electric field generated between the positive electrode and the negative electrode to the monitoring device 200. The detection IC 13 identifies the detection value corresponding to the electric field intensity in this way, which causes a reduction of the measurement error of the potential difference between the positive electrode and the negative electrode due to the influence of the line resistance, even if the distance between the electrode pair E including the positive electrode and the negative electrode and the monitoring device 200 is large.

Further, in the detection device 1, the plurality of detection ICs 13 corresponding to the plurality of electrode pairs E transmits the electric field intensity detection value to the relay substrate 20 via the same serial communication signal line. Therefore, even when the detection device 1 has a large number of electrode pairs E, the number of wirings to the monitoring device 200 can be reduced, so that the density with which the electrode pairs E are provided in the seat belt 100, which has a limited area, can be increased. As a result, the detection device 1 can increase the resolution in detecting the electric field intensity.

Second Embodiment

[A Detection Device Attachable to the Seat Belt]

In the first embodiment, the positive electrode 11 and the negative electrode 12 are provided on the seat belt 100, but the second embodiment is different from the first embodiment in that the positive electrode and the negative electrode are provided on a detection device 2 which is detachable from the seat belt.

Figure 23A:
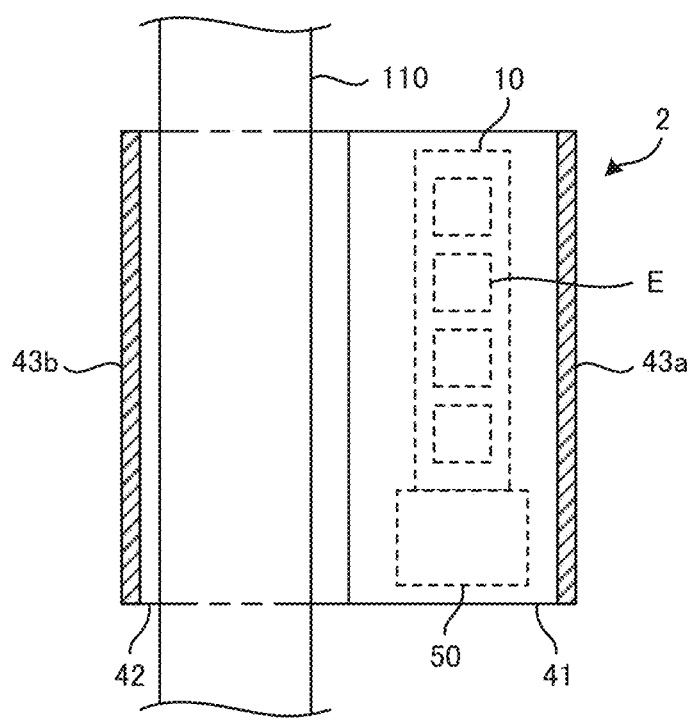
FIGS. 23A and 23B each schematically show a configuration example of a detection device according to the second embodiment.
Figure 23B:
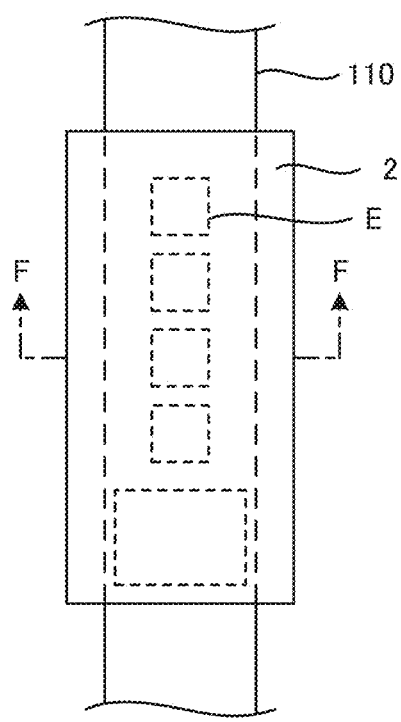
Figure 24:
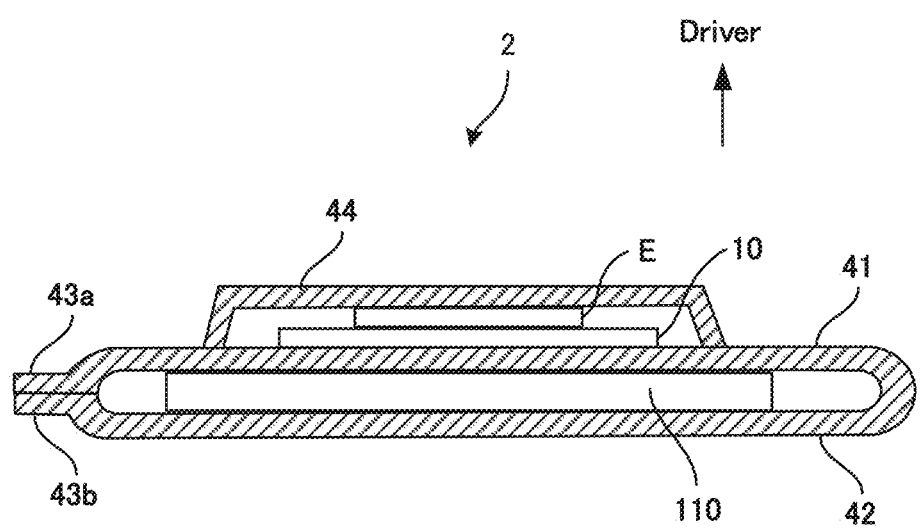
FIG. 24 is an F-F-line cross section of the detection device.
Figure 25A:
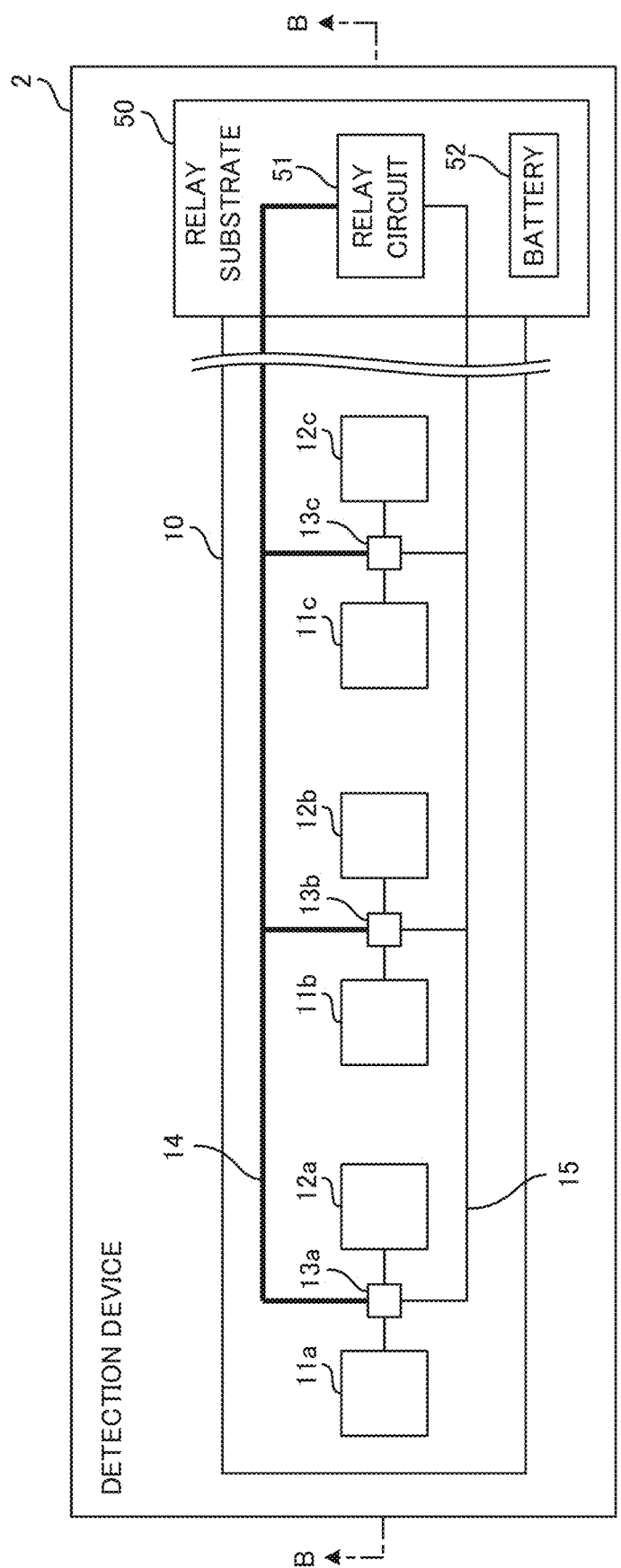
FIGS. 25A and 25B are each a schematic diagram showing a configuration of the detection device.
Figure 25B:
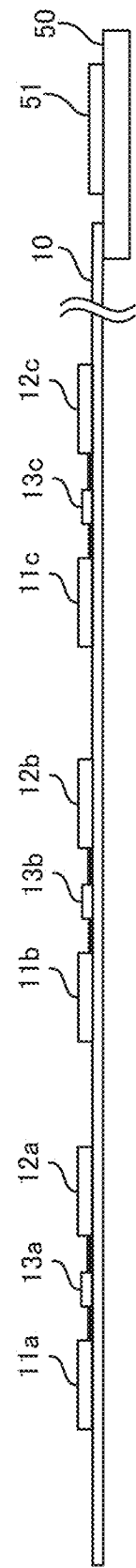

FIGS. 23A and 23B each schematically show a configuration example of the detection device 2 according to the second embodiment. FIG. 23A is a plane figure of the detection device 2 before being mounted on the seat belt 110. The detection device 2 includes a first region 41 and a second region 42. The first region 41 is a region provided with an electrode, a sensor, and a semiconductor element for detecting the state of the driver's body. FIG. 24 is an F-F-line cross section of the detection device 2 in the state shown in FIG. 23B. FIGS. 25A and 25B are each a schematic diagram showing a configuration of the detection device 2.

The detection device 2 includes, for example, the flexible substrate 10 and the relay substrate 50 provided in the first region 41. The flexible substrate 10 is equivalent to the flexible substrate 10 shown in the first embodiment, and may have the positive electrode 11, the negative electrode 12, and the detection IC 13 as shown in FIG. 3, or may have the positive electrode 31, the negative electrode 32, and the detection IC 13 as shown in FIG. 8, or may have the positive electrode 31, the negative electrode 32, the detection IC 16, and the shape sensor 17 as shown in FIG. 15. In any of these, the detection IC 13 and the detection IC 16 transmit, to the relay substrate 50, the digital data including the measurement value indicating the electric field intensity or the measurement value indicating the shape by a serial communication method such as SPI or I2C.

The relay substrate 50 transfers the digital data received from the flexible substrate 10 to the monitoring device 200, in a similar manner as the relay substrate 20. Since the detection device 2 is detachably mounted on the seat belt 110, it is preferable that the relay substrate 50 transmits the digital data to the monitoring device 200 using a wireless channel such as Bluetooth. Therefore, the relay substrate 50 includes a relay circuit 51 for converting the digital data received from the flexible substrate 10 into wireless data. The relay circuit 51 has a configuration similar to that of the relay circuit 21 shown in FIG. 6, but differs from the relay circuit 21 in that a communication part 215 has a wireless communication function for wirelessly transmitting the data indicating the electric field intensity detection value outputted from the detection IC 13 to an external device.

Further, a battery 52 is provided in the relay substrate 50 so that the relay substrate 50 can supply power to the element provided in the flexible substrate 10 even when the relay substrate 50 is not connected to the monitoring device 200 by a cable and the relay substrate 50 is not supplied with electric power. The battery 52 is, for example, a rechargeable secondary battery. The relay substrate 50 may have a wireless charging circuit so that the battery 52 can be charged without connecting the relay substrate 50 to a power outlet.

The first region 41 and the second region 42 are provided with fastening parts 43a and 43b such as hook and loop fasteners or buttons for fastening the first region 41 and the second region 42. The fastening parts 43a and 43b function as attaching parts for attaching the detection device 2 to the seat belt 110. A user, such as a driver or an employee of a company to which the driver belongs, folds the detection device 2 so as to sandwich the seat belt 110 between the first region 41 and the second region 42, and fastens the first region 41 and the second region 42 using the fastening parts 43a and 43b to realize a function equivalent to that of the detection device 1 of the first embodiment. It should be noted that, when the length of the detection device 2 is short, it is assumed that the shape of the seat belt does not sufficiently change depending on the state of the body (for example, the position of the chest). In this case, the movement of the body can be quantitatively detected by adding a sensor such as an acceleration sensor or a gyro sensor to the relay substrate 50 and the like.

As shown in FIG. 24, in the detection device 2, the electrode pair E is provided so as to generate the electric field on the surface facing the driver's body. That is, the electrode pair E is provided so as to be positioned on a surface of the flexible substrate 10 opposite to the surface provided with the second region 42 in a state where the detection device 2 is folded. Further, as shown in FIG. 24, the detection device 2 may include a cover 44 covering the flexible substrate 10 so that the flexible substrate 10 is not visually recognized.

Furthermore, in the above description, the configuration in which the flexible substrate 10 and the relay substrate 50 are provided in the first region 41 is illustrated, but the flexible substrate 10 and the relay substrate 50 may be provided to both of the first region 41 and the second region 42. If the detection device 2 is configured in this manner, the monitoring system S can monitor the state of the driver regardless of the direction in which the driver mounts the detection device 2 to the seat belt 110 or the surface on which the driver wears the seat belt 110.

In the second embodiment, the monitoring device 200 is not fixed to the vehicle and may be carried by the driver. Moreover, the monitoring device 200 may transmit the data received from the relay substrate 50 to other devices (for example, a computer).

A mark for alignment may be attached to the seat belt 110 so that a person wearing the seat belt 110 can mount the detection device 2 at a position on the seat belt 110 where the detection device 2 can easily detect the heartbeat or the breathing. The alignment mark is, for example, a mark for mounting the detection device 2 so that the center position of the detection device 2 aligns with the center position of the person's chest when the person is wearing the seat belt 110.

That is, the alignment mark is provided at a predetermined distance from the end of the seat belt 110. The predetermined distance is, for example, a distance obtained by adding or subtracting half the length of the detection device 2 in the longitudinal direction to the distance of the seat belt 110 from its end to the center position of the chest when the average person wears the seat belt 110. Such a mark is provided on the seat belt 110, and so the detection device 2 can improve the accuracy in detecting the state of the body of the person wearing the seat belt 110.

The seat belt 110 may be provided with a fastening member for the detection device 2 to be fastened at a predetermined position of the seat belt 110, together with or instead of the mark. The fastening member is, for example, a snap button to be fastened to a snap button provided on the detection device 2, or a hook and loop fastener to be fastened to a hook and loop fastener provided on the detection device 2.

[Effect Realized by the Detection Device 2]

The detection device 2 is configured to be detachable from the seat belt 110, and when the driver wears the seat belt 110 with the detection device 2 attached to the seat belt 110, the detection device 2 can transmit a signal indicating the state of the driver's body to the monitoring device 200. The detection device 2 is configured to be detachable from the seat belt 110 in this way, the monitoring system S can monitor the state of the driver by mounting the detection device 2 on the seat belt 110, even in a vehicle without the detection device 1.

<Variations>

[A Variation of an Electric Element]

In the above description, the detection device provided with the electrode pair E, which generates the electric field, as an electric element whose electrical characteristics change according to the movement of the person's body is exemplified, but the electrode pair E does not have to be provided in the detection device. In this case, for example, the detection device is provided with a curvature sensor, as an electric element, whose impedance changes according to the curvature of the base material. In this instance, the detection IC as a semiconductor element detects the impedance of the curvature sensor, and outputs the value of the detected impedance.

Figure 26:
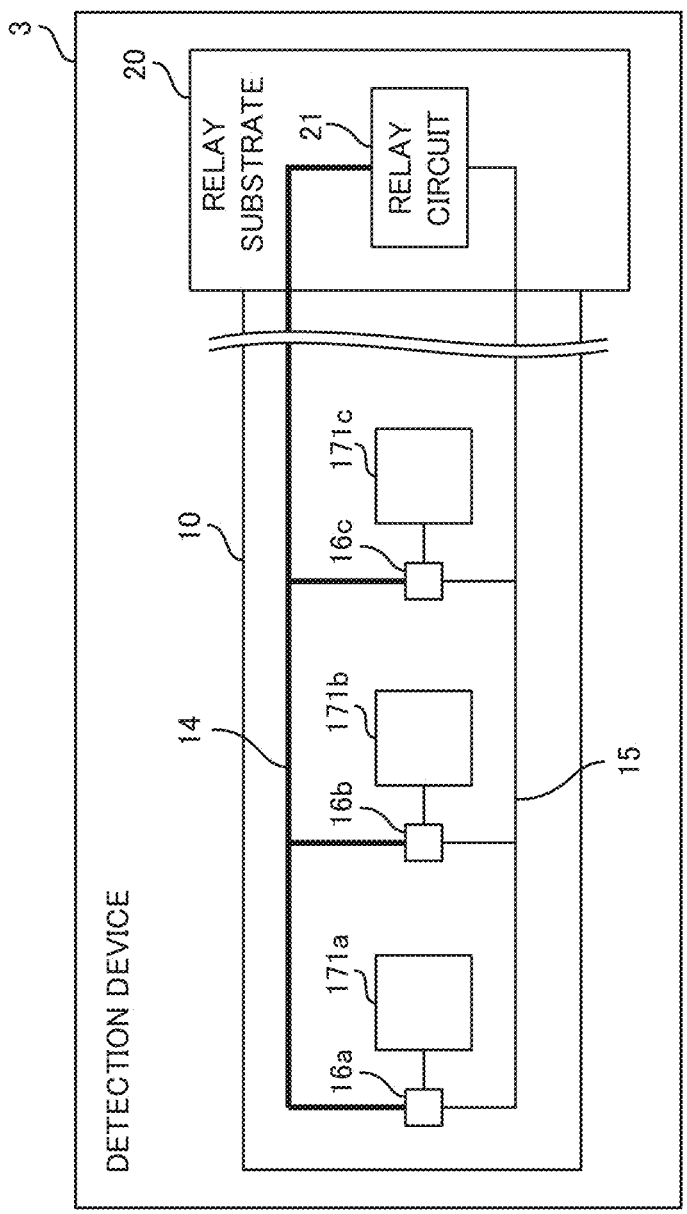
FIG. 26 shows a configuration of a detection device as a variation.

FIG. 26 shows a configuration of a detection device 3 as a variation. The detection device 3 includes the flexible substrate 10, as a base material, and the plurality of curvature sensors 171 (curvature sensors 171a to 171c in FIG. 26) provided on the flexible substrate 10. The curvature sensors 171 are provided at different positions along the longitudinal direction of the flexible substrate 10. For example, the plurality of curvature sensors 171 is provided such that adjacent curvature sensors 171 are provided in different directions from each other. The impedance of the curvature sensor 171 changes according to the curvature. Therefore, the impedance of the curvature sensor 171 changes as the curvature of the flexible substrate 10 changes in accordance with the movement of the person.

The detection ICs 16 (a detection IC 16a to a detection IC 16c in FIG. 26) for detecting the impedances of the curvature sensors 171 and outputting the detection values corresponding to the detected results are respectively provided in the vicinity of the plurality of curvature sensors 171. As described above, in the detection device 3, the detection ICs 16 are respectively provided in the vicinity of the plurality of curvature sensors 171, and so the impedances of the curvature sensors 171 can be detected with high accuracy, which makes it possible to detect minute movements such as the breathing or the heartbeat of a person without using the electrode pair E.

The detection device 3 includes the relay substrate 20 in a similar manner as the detection device 1 shown in FIG. 3. Further, the power supply pattern 14 and the signal pattern 15 are formed in the flexible substrate 10 in a similar manner as in the flexible substrate 10 shown in FIG. 3.

[Types of Substrates]

In the above description, the flexible substrate 10 is exemplified as the base material, but other members may be used as the base material. For example, the base material may be a cloth-like member composed of fibers. In this instance, the base material is a cloth-like member made by knitting a non-conductive fiber and a conductive fiber for transmitting electrical signals, and the conductive fiber is used as the power supply pattern 14 and the signal pattern 15. Further, the conductive fiber knitted into the base material in a rectangular shape may be used as the electrode pair E.

Further, apart of the non-conductive fiber may be composed of a fiber functioning as a curvature sensor whose impedance changes according to the curvature. The fiber which functions as a curvature sensor is configured as a fiber in which, for example, a conductive fiber is spirally wound around a linear polymer. In this case, the detection IC may be provided on the cloth-like member, but the detection IC does not have to be provided. In this manner, a cloth-like member including a fiber as the base material, and the fiber constituting the cloth-like member function as the curvature sensor, whereby the thickness of the detection device can be reduced.

Further, in the above description, a case where the relay substrate 20 and the relay substrate 50 are separated from the flexible substrate 10 is exemplified, but the relay substrate 20 and the relay substrate 50 may be integrated into the flexible substrate 10, and components mounted on the relay substrate 20 and the relay substrate 50 may be mounted on the flexible substrate 10. Conversely, components mounted on the flexible substrate 10 may be mounted on the relay substrate 20 and the relay substrate 50.

The present disclosure is explained on the basis of the exemplary embodiments. The technical scope of the present disclosure is not limited to the scope explained in the above embodiments and it is possible to make various changes and modifications within the scope of the disclosure. For example, the specific embodiments of the distribution and integration of the apparatus are not limited to the above embodiments, all or part thereof, can be configured with any unit which is functionally or physically dispersed or integrated. Further, new exemplary embodiments generated by arbitrary combinations of them are included in the exemplary embodiments of the present disclosure. Further, effects of the new exemplary embodiments brought by the combinations also have the effects of the original exemplary embodiments.

For example, in the above description, a case where the detection device is provided in the seat belt to identify the state of the driver's body is exemplified, but the configuration and the application of the detection device are not limited thereto. The present disclosure can be applied to a detection device of any aspect which is wearable on a human body.

Further, the positive electrode, the negative electrode, the shape sensor, and the various wirings are not limited to the above-described embodiments. The positive electrode, the negative electrode, the shape sensor, and the various wirings may be formed of conductive fibers, for example.

Furthermore, in the above description, a case where the detection device is provided with the plurality of detection ICs, the plurality of electrode pairs, or the plurality of curvature sensors is exemplified, but the configuration of the detection device is not limited to such a configuration. The detection device may include one electrode pair and one detection IC 13 for detecting a change in the electric field caused by said electrode pair. In addition, the detection device may include one curvature sensor 171 and one detection IC 16 for detecting a change in a voltage or a current with the curvature sensor 171.

What is claimed is:

1. A detection device for detecting movement of a human body, comprising:
   a base material that has flexibility;
   a plurality of electric elements that are provided on the base material and whose electrical characteristics change according to the movement of the human body; and
   a plurality of semiconductor elements that are provided on the base material, the semiconductor elements being connected to the plurality of electric elements, each detects a change in the electrical characteristics of the corresponding electric element, and transmits digital data showing a detection value corresponding to detected result via the same serial signal line.

2. The detection device according to claim 1, wherein each of the plurality of semiconductor elements is provided at a position closer to the electric element corresponding to the semiconductor element than to the electric element corresponding to other semiconductor elements.

3. The detection device according to claim 1, wherein a plurality of distances between each of the plurality of semiconductor elements and the electric element corresponding respectively to the plurality of semiconductor elements are the same.

4. The detection device according to claim 1, comprising:
a curvature sensor, as the electric element, whose impedance changes according to the curvature of the base material, wherein
the semiconductor element detects impedance of the curvature sensor and outputs a value of the detected impedance.

5. The detection device according to claim 4, wherein a plurality of the curvature sensors are provided in different directions at different positions along a longitudinal direction of the base material.

6. The detection device according to claim 1, comprising, as the electric element:
a positive electrode that is provided on the base material;
a negative electrode that is different from the positive electrode; and
an electric field generator that generates an electric field between the positive electrode and the negative electrode, wherein
the semiconductor element outputs an electric field intensity detection value corresponding to an intensity of an electric field generated between the positive electrode and the negative electrode.

7. The detection device according to claim 6, wherein the negative electrode is smaller than the positive electrode, and the positive electrode and the negative electrode are provided on the base material so that a projection surface of the negative electrode in a thickness direction of the base material is included within a region surrounded by the contour of the positive electrode.

8. The detection device according to claim 6, wherein the positive electrode surrounds the negative electrode in a region excluding a position where wiring for connecting the negative electrode and the semiconductor element is provided.

9. The detection device according to claim 6, further comprising:
a guard electrode that is provided on a surface of the base material opposite to a surface on which the positive electrode and the negative electrode are provided; and
a potential adjustment circuit that makes the potential of the guard electrode the same as that of the negative electrode.

10. The detection device according to claim 6, comprising:
a plurality of the positive electrodes;
a plurality of the negative electrodes;
the plurality of semiconductor elements that outputs the electric field intensity detection value corresponding to an intensity of an electric field generated between one of the plurality of positive electrodes and one of the plurality of negative electrodes; and
a controller that controls the plurality of semiconductor elements so as to obtain the electric field intensity detection value corresponding to an intensity of an electric field generated between one positive electrode selected from the plurality of positive electrodes and one negative electrode selected from the plurality of negative electrodes.

11. The detection device according to claim 1, comprising, as the electric element:

a curvature sensor whose impedance changes according to a curvature of the base material;
a positive electrode that is provided on the base material;
a negative electrode that is different from the positive electrode; and
an electric field generator that generates an electric field between the positive electrode and the negative electrode, wherein
the semiconductor element executes a) a detection process of an intensity of an electric field generated between the positive electrode and the negative electrode and b) the detection process of the impedance, while switching in a time-division manner.

12. The detection device according to claim 11, wherein the curvature sensor is provided on at least one of the positive electrode or the negative electrode.

13. The detection device according to claim 1, further comprising:
an attaching part for attaching the detection device to the seat belt mounted on the vehicle; and
a communication part that wirelessly transmits data indicating an electric field intensity detection value outputted from the semiconductor element to an external device.

14. The detection device according to claim 1, wherein each of the plurality of semiconductor elements transmits the digital data including the detection value at the time when, each of the plurality of semiconductor elements receives a command with an address of the semiconductor element from a relay substrate.

15. The detection device according to claim 14, wherein the plurality of semiconductor elements detect the change of the electrical characteristics simultaneously on the basis of a control signal inputted from the relay substrate, each of the plurality of semiconductor elements temporarily holds the detection value until when the semiconductor element transmits the detection value.

16. A seat belt mounted on a vehicle, comprising:
a strip-shaped front-side belt;
a reverse-side belt that is coupled with the front-side belt; and
a detection device that is provided between the front-side belt and the reverse-side belt, wherein
the detection device includes
a base material that has flexibility,
a plurality of electric elements that are provided on the base material, and whose electrical characteristics change according to movement of a human body; and
a plurality of semiconductor elements that are provided on the base material, the semiconductor elements being connected to the plurality of electric elements, each detects a change in the electrical characteristics of the corresponding electric element, and transmits digital data showing a detection value corresponding to detected result via the same signal line.

17. A monitoring system comprising:
a detection device that detects a state of a person wearing a seat belt mounted on a vehicle; and
a monitoring device that controls the vehicle on the basis of the state of the person detected by the detection device, wherein
the detection device includes
a base material that has flexibility,
a plurality of electric elements that are provided on the base material, and whose electrical characteristics change according to the movement of the human body, a plurality of semiconductor elements that are provided on the base material, the semiconductor elements being connected to the plurality of electric elements, each detects a change in the electrical characteristics of the corresponding electric element, and transmits digital data showing a detection value corresponding to detected result via the same serial line, and a transmission part that transmits signals including the detection value outputted by the semiconductor element to the monitoring device.

* * * * *